United States Patent
Ishikawa et al.

(10) Patent No.: US 11,160,451 B2
(45) Date of Patent: Nov. 2, 2021

(54) APPARATUS, METHOD, PROGRAM, AND SYSTEM

(71) Applicant: Sony Olympus Medical Solutions Inc., Tokyo (JP)

(72) Inventors: Tomonori Ishikawa, Tokyo (JP); Naobumi Okada, Saitama (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 259 days.

(21) Appl. No.: 16/349,299

(22) PCT Filed: Sep. 8, 2017

(86) PCT No.: PCT/JP2017/032403
§ 371 (c)(1),
(2) Date: May 13, 2019

(87) PCT Pub. No.: WO2018/096763
PCT Pub. Date: May 31, 2018

(65) Prior Publication Data
US 2020/0178795 A1   Jun. 11, 2020

(30) Foreign Application Priority Data
Nov. 22, 2016   (JP) .............................. JP2016-226651

(51) Int. Cl.
*A61B 3/13* (2006.01)
*A61B 90/25* (2016.01)
(Continued)

(52) U.S. Cl.
CPC .............. *A61B 3/13* (2013.01); *A61B 3/0075* (2013.01); *A61B 3/14* (2013.01); *A61B 90/25* (2016.02); *A61B 2505/05* (2013.01)

(58) Field of Classification Search
CPC .... A61B 3/10; A61B 3/12; A61B 3/13; A61B 3/14
(Continued)

(56) References Cited

U.S. PATENT DOCUMENTS

| | | |
|---|---|---|
| 5,793,524 A | 8/1998 | Luloh |
| 6,943,942 B2 | 9/2005 | Horiguchi et al. |

(Continued)

FOREIGN PATENT DOCUMENTS

| | | |
|---|---|---|
| CN | 1447146 A | 10/2003 |
| CN | 105852798 A | 8/2016 |

(Continued)

OTHER PUBLICATIONS

Extended European Search Report dated Oct. 22, 2019, issued in corresponding European Patent Application No. 17873303.6.
(Continued)

*Primary Examiner* — Hung X Dang
(74) *Attorney, Agent, or Firm* — Xsensus LLP

(57) ABSTRACT

Provided is a microscope apparatus including: a microscope section configured to image a subject's eye with an image sensor for performing magnified observation of the subject's eye; a holding section configured to hold the microscope section; a front lens insertion/removal unit configured to insert/remove a front lens for observing a posterior eye of the subject's eye onto an optical axis of the microscope section; and a control apparatus configured to execute an AF control that focuses the microscope section on an image-forming position of an image of the posterior eye by the front lens when the front lens is inserted onto the optical axis of the microscope section by the front lens insertion/removal unit.

18 Claims, 8 Drawing Sheets

(51) Int. Cl.
*A61B 3/00* (2006.01)
*A61B 3/14* (2006.01)

(58) Field of Classification Search
USPC .................................. 351/206, 205, 246, 200
See application file for complete search history.

(56) References Cited

U.S. PATENT DOCUMENTS

| | | | |
|---|---|---|---|
| 2006/0203330 A1* | 9/2006 | Moeller | A61B 3/13 |
| | | | 359/377 |
| 2008/0084540 A1* | 4/2008 | Gaida | A61B 3/13 |
| | | | 351/216 |
| 2013/0070076 A1 | 3/2013 | Kuster | |
| 2014/0146287 A1 | 5/2014 | Ota | |
| 2015/0335242 A1 | 11/2015 | Saito | |

FOREIGN PATENT DOCUMENTS

| | | |
|---|---|---|
| EP | 2 730 214 A1 | 5/2014 |
| EP | 2 835 097 A1 | 2/2015 |
| JP | 2006-247399 A | 9/2006 |
| JP | 2008-093433 A | 4/2008 |
| JP | 2009-205156 A | 9/2009 |
| WO | 2009/051052 A1 | 4/2009 |
| WO | 2016/040935 A1 | 3/2016 |

OTHER PUBLICATIONS

International Search Report and Written Opinion dated Nov. 28, 2017 for PCT/JP2017/032403 filed on Sep. 8, 2017, 10 pages including translation of the International Search Report.

* cited by examiner

APPARATUS, METHOD, PROGRAM, AND SYSTEM

CROSS-REFERENCE TO RELATED APPLICATIONS

The present application is based on PCT filing PCT/JP2017/032403 filed Sep. 8, 2017 which claims priority to JP 2016-226651 filed Nov. 22, 2016, the entire contents of each are incorporated herein by reference.

TECHNICAL FIELD

The present invention relates to an apparatus, a method, a program, and a system for doing this and that.

BACKGROUND ART

The microscope apparatus is configured such that a microscope section including an observation optical system for magnified observation of the subject's eye is held by an arm section (holding section).

Herein, in eye surgery, in some cases there arises a need to appropriately switch between observation (for example, observation of the crystalline lens) of the anterior eye (the part on the front side from the crystalline lens of the subject's eye) and observation (for example, observation of the fundus (retina)) of the posterior eye (the part farther back than the crystalline lens of the subject's eye) during surgery. For this reason, even microscope apparatus are being developed with a front lens insertable and removable from the optical axis of the microscope section between the microscope section and the subject's eye. When observing the anterior eye, the front lens is removed from the optical axis of the microscope section, and when observing the posterior eye, the front lens is inserted onto the optical axis of the microscope section. Note that in the following description, in the case of simply stating the "optical axis", unless particularly noted otherwise, the statement means the optical axis of the microscope section of the microscope apparatus.

For example, Patent Literature 1 discloses a front lens insertion/removal unit configured separately from the microscope section and used by being attached to the operating table for example. Also, for example, Patent Literature 2 and 3 disclose front lens insertion/removal units that are integrated with the microscope section by being attached to the microscope section.

CITATION LIST

Patent Literature

Patent Literature 1: U.S. Pat. No. 5,793,524
Patent Literature 2: U.S. Pat. No. 6,943,942
Patent Literature 3: JP 2009-205156A

DISCLOSURE OF INVENTION

Technical Problem

At this point, when the front lens is removed from the optical axis and the anterior eye is observed, the focal point of the microscope section is on the anterior eye that is the observation target. In the case in which the front lens is inserted onto the optical axis in this state, since a clear image of the posterior eye is not obtained directly, it is necessary to refocus. Even with the technologies described in Patent Literature 1 to 3, work for refocusing may occur, such as moving the position of the microscope section in the optical axis direction (Patent Literature 2) and additionally inserting another lens onto the optical axis (Patent Literature 3), for example.

In the technologies described in Patent Literature 1 to 3, such work for refocusing is performed manually. Consequently, this troublesome work becomes a large burden on the medical staff such as the surgeon and an assistant. Also, if surgery is interrupted by such work, smooth surgery is impeded, leading to an increase in the surgery time.

Accordingly, the present disclosure proposes and novel and improved microscope apparatus and control method making it possible to perform eye surgery more smoothly.

Solution to Problem

According to the present disclosure, there is provided a microscope apparatus including: a microscope section configured to image a subject's eye with an image sensor for performing magnified observation of the subject's eye; a holding section configured to hold the microscope section; a front lens insertion/removal unit configured to insert/remove a front lens for observing a posterior eye of the subject's eye onto an optical axis of the microscope section; and a control apparatus configured to execute an AF control that focuses the microscope section on an image-forming position of an image of the posterior eye by the front lens when the front lens is inserted onto the optical axis of the microscope section by the front lens insertion/removal unit.

Moreover, according to the present disclosure, there is provided a control method, executed by a processor, including: when performing magnified observation of a subject's eye using a microscope apparatus provided with a microscope section configured to image the subject's eye with an image sensor for performing magnified observation of the subject's eye, a holding section configured to hold the microscope section, and a front lens insertion/removal unit configured to insert/remove a front lens for observing a posterior eye of the subject's eye onto an optical axis of the microscope section, executing an AF control that focuses the microscope section on an image-forming position of an image of the posterior eye by the front lens when the front lens is inserted onto the optical axis of the microscope section by the front lens insertion/removal unit.

According to the present disclosure, in a microscope apparatus used for eye surgery, when a front lens for observing the posterior of the subject's eye is inserted onto the optical axis of a microscope section, an AF control that focuses the microscope section on an image-forming position of an image of the posterior eye by the front lens is executed. Consequently, since it is not necessary to manually perform the work for refocusing associated with the insertion of the front lens, it becomes possible to perform surgery more smoothly.

Advantageous Effects of Invention

According to the present disclosure described above, it is possible to perform eye surgery more smoothly. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
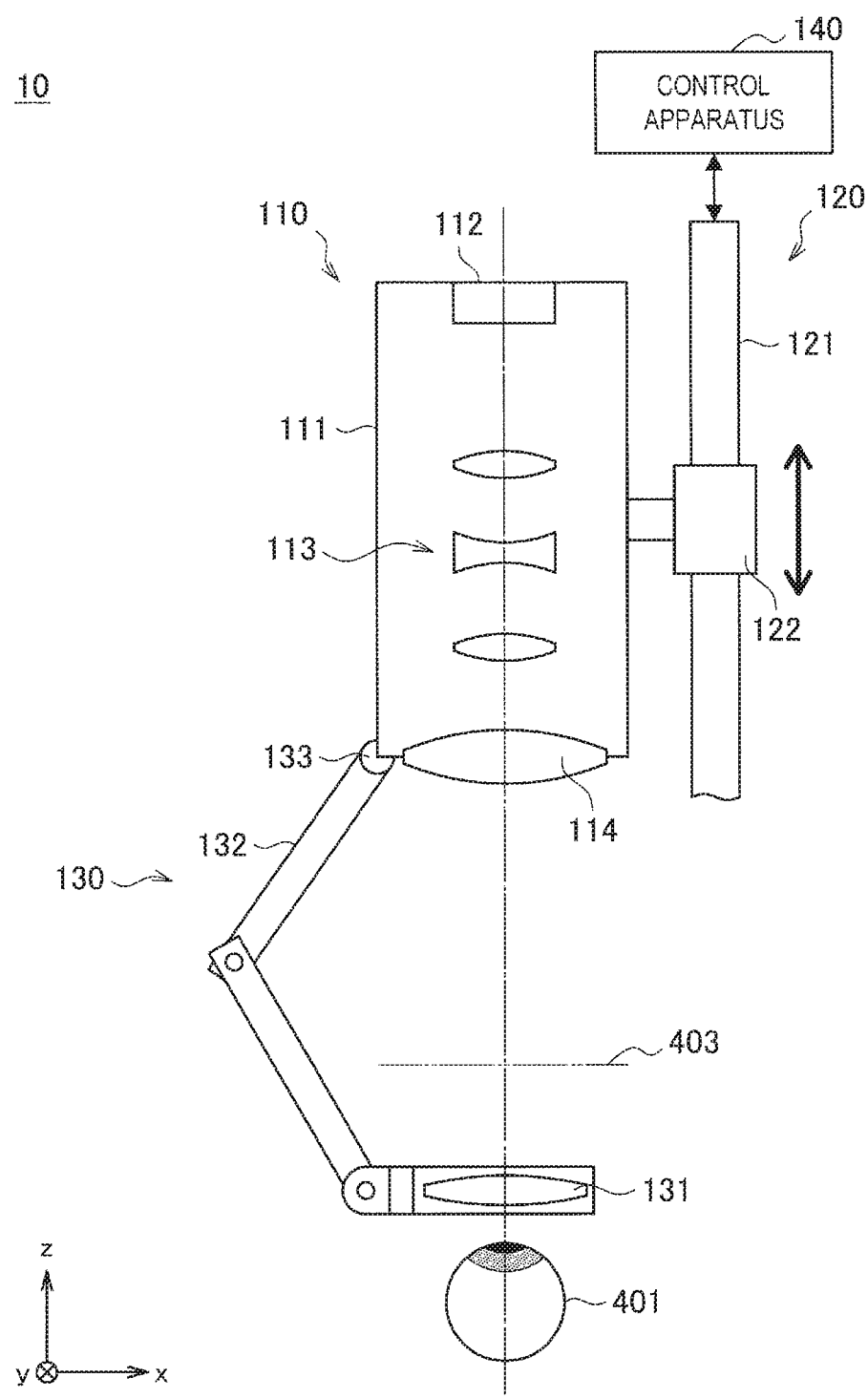
FIG. 1 is a diagram illustrating a schematic configuration of a microscope apparatus according to a first embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that in each of the diagrams illustrated in this specification, the apparent sizes of some component members are exaggerated in some cases for the sake of explanation. The relative sizes of the respective members illustrated in each of the drawings do not necessarily represent accurately the size relationships among actual members.

Also, in the following description, the vertical direction is defined to be the z-axis direction. The z-axis direction is also called the up-and-down direction. Also, the two mutually orthogonal directions in the plane (horizontal plane) orthogonal to the z-axis direction are also called the x-axis direction and the y-axis direction, respectively. The direction parallel to the x-y plane is also called the horizontal direction.

Also, in the present disclosure, in the observation of a subject's eye, the target site of the observation is switched between the anterior eye and the posterior eye, and the following description takes as an example a case in which the observation target site of the posterior eye is the fundus (retina). However, the present disclosure is not limited to such an example, and the observation target site of the posterior eye may also be another site such as the vitreous body for example.

Hereinafter, the description will proceed in the following order.

1. First Embodiment
   1-1. Configuration of microscope apparatus
   1-2. Functional configuration of control apparatus
   1-3. Control method
   1-4. Modification
      1-4-1. Overall configuration of microscope apparatus
      1-4-2. Functional configuration of control apparatus
      1-4-3. Control method
2. Second Embodiment
   2-1. Configuration of microscope apparatus
   2-2. Functional configuration of control apparatus
   2-3. Control method
3. Supplement FIG. 1 will be referenced to describe a configuration of the microscope apparatus according to the first embodiment. FIG. 1 is a diagram schematically illustrating a configuration of the microscope apparatus according to the first embodiment.

Referring to FIG. 1, the microscope apparatus 10 according to the first embodiment is provided with a microscope section 110 for performing magnified observation of a subject's eye 401, an arm section 120 (holding section 120) that holds the microscope section 110, a front lens insertion/removal unit 130 that inserts or removes a front lens on the optical axis of the microscope section 110, and a control apparatus 140 that centrally controls the operations of the microscope apparatus 10.

Herein, during eye surgery, normally a patient lies supine on top of an operating table with one's eyes (that is, the subject's eye 401) facing directly above. Additionally, the microscope section 110 is disposed directly above the subject's eye 401 such that the optical axis is parallel to an approximately vertical direction, and the subject's eye 401 is observed by the microscope section 110. In the following, the microscope apparatus 10 is described as one in which the microscope section 110 is disposed with respect to the subject's eye 401 in such a state and the optical axis of the microscope section 110 is approximately parallel to the vertical direction.

The microscope section 110 includes a housing 111, an image sensor 112 provided inside the housing 111, an optical system 113 provided inside the housing 111, and an objective lens 114. In FIG. 1, for the sake of explanation, a cross-sectional view cutting the microscope section 110 along a plane passing through the optical axis is illustrated schematically.

The housing 111 has an approximately cylindrical shape that is open at one end. The housing 111 is disposed such that the opening faces downward, and the objective lens 114 is fitted into the opening. The image sensor 112 is disposed at the site of the floor corresponding to the top end of the housing 111. Also, the optical system 113 is disposed in front of the image sensor 112.

During observation of the subject's eye 401, the microscope section 110 is disposed such that the objective lens 114 opposes the subject's eye 401 directly above the subject's eye 401. Inside the housing 111, a light source and an optical system (illumination optical system) not illustrated are provided, and during observation, illuminating light is radiated from the light source, through the objective lens 114, and onto the subject's eye 401. Of the illuminating light, reflected light (observation light) from the subject's eye 401 enters the housing 111 through the objective lens 114. The observation light entering the housing 111 passes through the optical system 113 and is condensed onto the image sensor 112.

The optical system 113 is a combination of components, the optical characteristics of which are designed such that observation light forms an image on the light-sensitive face of the image sensor 112. The configuration of the optical system 113 is not limited to the illustrated example, and may be configured in any way having optical characteristics such that the observation light forms an image on the light-sensitive face of the image sensor 112.

The image sensor 112 receives and photoelectrically converts the observation light to thereby generate a signal corresponding to the observation light, or in other words, an image signal corresponding to the observed image. The image sensor 112 transmits the generated image signal to the control apparatus 140. For the image sensor, any of various known types of image sensors may be used, such as a complementary metal-oxide-semiconductor (CMOS) image sensor or a charge-coupled device (CCD) image sensor.

In this way, the microscope section 110 is an electronic imaging microscope section that electronically captures an image with the image sensor 112. In surgery using the microscope apparatus 10 provided with the electronic imaging microscope section 110 (hereinafter also called the electronic imaging microscope apparatus 10), a display apparatus not illustrated is installed in a location visible to the surgeon, such as on a wall of the operating room for example, and under control from the control apparatus 140, the image captured by the microscope section 110 is made to appear on the display apparatus. The surgeon performs various treatments on the subject's eye 401 while observing the subject's eye 401 through the image appearing on the display apparatus.

The microscope section 110 is provided with a driving mechanism (not illustrated) that moves the zoom lens and the focus lens of the optical system 113 along the optical axis. By suitably moving the zoom lens and the focus lens with the driving mechanism under control from the control apparatus 140, the magnification of the captured image and the focal length during imaging may be adjusted. In the first embodiment, the microscope section 110 includes an auto-focus (AF) function, and is configured to be able to adjust the focal length automatically.

Note that the configuration of the microscope section 110 is not limited to the one described above, and the microscope section 110 preferably includes a configuration similar to a typical electronic zoom microscope section. For example, the microscope section 110 may be provided with any of various types of functions typically provided in an electronic imaging microscope section, such as an auto-exposure (AE) function and an electronic zoom function.

The holding section 120 includes a stand 121 that extends in the vertical direction, and a linear motion mechanism 122 that holds the microscope section 110 and is also capable of moving over the stand 121 along the stand 121. Although omitted from illustration, the base end of the stand 121 is secured to the operating table on which the patient lies supine, the floor of the operating room, or the like, for example. The linear motion mechanism 122 is provided near the front end of the stand 121, and the microscope section 110 is held by the linear motion mechanism 122. In other words, because of the linear motion mechanism 122, the holding section 120 includes a function of holding the microscope section 110 movably in the vertical direction, or in other words, in the optical axis direction of the microscope section 110 during observation of the subject's eye 401. The linear motion mechanism 122 is provided with an actuator, and by driving the actuator under control from the control apparatus 140, the linear motion mechanism 122 moves in the vertical direction.

The front lens insertion/removal unit 130 includes a front lens 131, a front lens holding member 132 that holds the front lens 131 on the front end, and a rotation axis section 133 interposed between the base end of the front lens holding member 132 and the microscope section 110 that rotatably supports the front lens holding member 132 with respect to the microscope section 110 by treating the base end of the front lens holding member 132 as a base point. Herein, a rotation axis section is used for convenience as a collective term for a member that forms a rotation axis. For example, the rotation axis section may include a bearing and a shaft rotatably inserted into the bearing or the like.

When observing the posterior eye (as described above, this is taken to be the fundus as one example herein), the front lens 131 is inserted onto the optical axis of the microscope section 110 between the microscope section 110 and the subject's eye 401. The optical characteristics of the front lens 131 are designed such that when the front lens 131 is disposed a predetermined distance from the subject's eye 401, a fundus image of the subject's eye 401 is formed at a predetermined position on the optical axis. In the following, the image-forming position of the fundus image by the design of the front lens 131 on the optical axis is also referred to as the designed fundus image position 403. Also, the state in which the image-forming position of the fundus image by the front lens 131 is aligned with the designed fundus image position 403 (that is, the position a predetermined distance from the subject's eye 401) is also referred to as the designed front lens position.

When the front lens 131 is used, the front lens 131 is disposed at the designed front lens position such that the image-forming position of the fundus image by the front lens 131 is aligned with the designed fundus image position 403. In this state, if the microscope section 110 is focused on the designed fundus image position 403, a clear image of the fundus will be observed. In the first embodiment, as described later, the process of disposing the front lens 131 and refocusing is executed automatically by the control apparatus 140.

The front lens holding member 132 includes a multi-link structure in which multiple links are successively joined to each other. The front lens 131 is held on the front end of the front lens holding member 132. Also, the base end of the front lens holding member 132 is connected to the outer wall of the housing 111 of the microscope section 110 through the rotation axis section 133.

According to such a configuration, the front lens holding member 132 is capable of rotating by the rotation axis section 133 with respect to the microscope section 110 by treating the base end as a base point. By having the front lens holding member 132 rotate with respect to the microscope section 110, the insertion and removal of the front lens 131 on the optical axis is realized (FIG. 1 illustrates a situation in which the front lens 131 is inserted onto the optical axis). The rotation axis section 133 is provided with an actuator, and by driving the actuator under control from the control apparatus 140, such rotation operation of the front lens holding member 132, or in other words, the insertion and removal of the front lens 131 on the optical axis, is executed.

Note that in the exemplary configuration illustrated in FIG. 1, the front lens insertion/removal unit 130 is configured such that in the case in which the front lens 131 is inserted onto the optical axis, the distance in the optical axis direction between the microscope section 110 and the front lens 131 becomes a fixed value. In other words, the length of the front lens holding member 132 is fixed.

The control apparatus 140 includes a processor such as a central processing unit (CPU) or a digital signal processor (DSP), or a control board or the like on which these processors and a storage element such as memory are mounted together. As a result of a processor included in the control apparatus 140 executing computational processing in accordance with a predetermined program, each function in the control apparatus 140 is realized. Note that in FIG. 1, to avoid complexity in the drawing, an arrow is drawn between the control apparatus 140 and the stand 121 of the holding section 120 to denote the connection between the two for the sake of convenience, but in actuality, the control apparatus 140 is connected to each member of the microscope apparatus 10 to allow the exchange of various information by any of various known types of wired or wireless communication methods.

The control apparatus 140 includes a function of controlling the operations of the microscope apparatus 10. Specifically, the control apparatus 140 causes the optical system 113 of the microscope section 110 to operate appropriately, and includes a function of adjusting the magnification and the focal length of the microscope section 110. In addition, the control apparatus 140 includes a function of performing various types of image processing on an image signal acquired by the microscope section 110, and causing the display apparatus to display an image based on the processed image signal. In other words, the control apparatus 140 also functions as a camera control unit (CCU).

Also, the control apparatus 140 includes a function of controlling the operations of the holding section 120. Specifically, the control apparatus 140 causes the linear motion mechanism 122 of the holding section 120 to operate appropriately, and moves the microscope section 110 in the optical axis direction.

Also, the control apparatus 140 includes a function of controlling the operations of the front lens insertion/removal unit 130. Specifically, by causing the rotation axis section 133 to operate and causing the front lens holding member 132 to rotate with respect to the microscope section 110, the control apparatus 140 executes the insertion or removal of the front lens 131 on the optical axis.

The control of the microscope section 110, the holding section 120, the front lens insertion/removal unit 130, and the display apparatus by the control apparatus 140 described above is executed in accordance with instruction input by the surgeon, for example. The microscope apparatus 10 is provided with an input apparatus such as a footswitch and a touch panel not illustrated, and by having the surgeon perform various types of instruction input through the input apparatus, the control apparatus 140 causes each configuration above to operate in accordance with the instruction input. For example, when observing the anterior eye, by instruction input through the input apparatus, the surgeon is able to dispose the microscope section 110 at a free position on the optical axis within the range of the working distance (WD).

At this point, in the microscope apparatus 10, the case of proceeding from the state of observing the anterior eye to the state of observing the posterior eye will be considered. In the state of observing the anterior eye, the front lens 131 is removed from the optical axis by the front lens insertion/removal unit 130, and the microscope section 110 is focused on the observation target site, namely the anterior of the subject's eye 401.

When proceeding to the state of observing the posterior eye, in the above state, the front lens 131 is inserted onto the optical axis by the front lens insertion/removal unit 130. At this time, as described above, since the front lens 131 is configured such that when disposed at the predetermined designed front lens position, a fundus image may be formed at the predetermined designed fundus image position 403, to observe the fundus image clearly, it is necessary to adjust the position in the optical axis direction of the front lens 131 and also adjust the focal length such that the microscope section 110 is focused on the designed fundus image position 403.

In the first embodiment, when the front lens 131 is inserted onto the optical axis, the refocusing process is executed automatically under control from the control apparatus 140. In existing typical microscope apparatus such as the technologies described in Patent Literature 1 to 3 described above, since such a refocusing process is performed manually, this troublesome work becomes an impediment to the smooth execution of surgery. In contrast, according to the first embodiment, since such a refocusing process is executed automatically as above, smoother surgery may be realized.

Hereinafter, functions related to the refocusing process in the control apparatus 140 will be described in detail.

(1-2. Functional Configuration of Control Apparatus)

Figure 2:
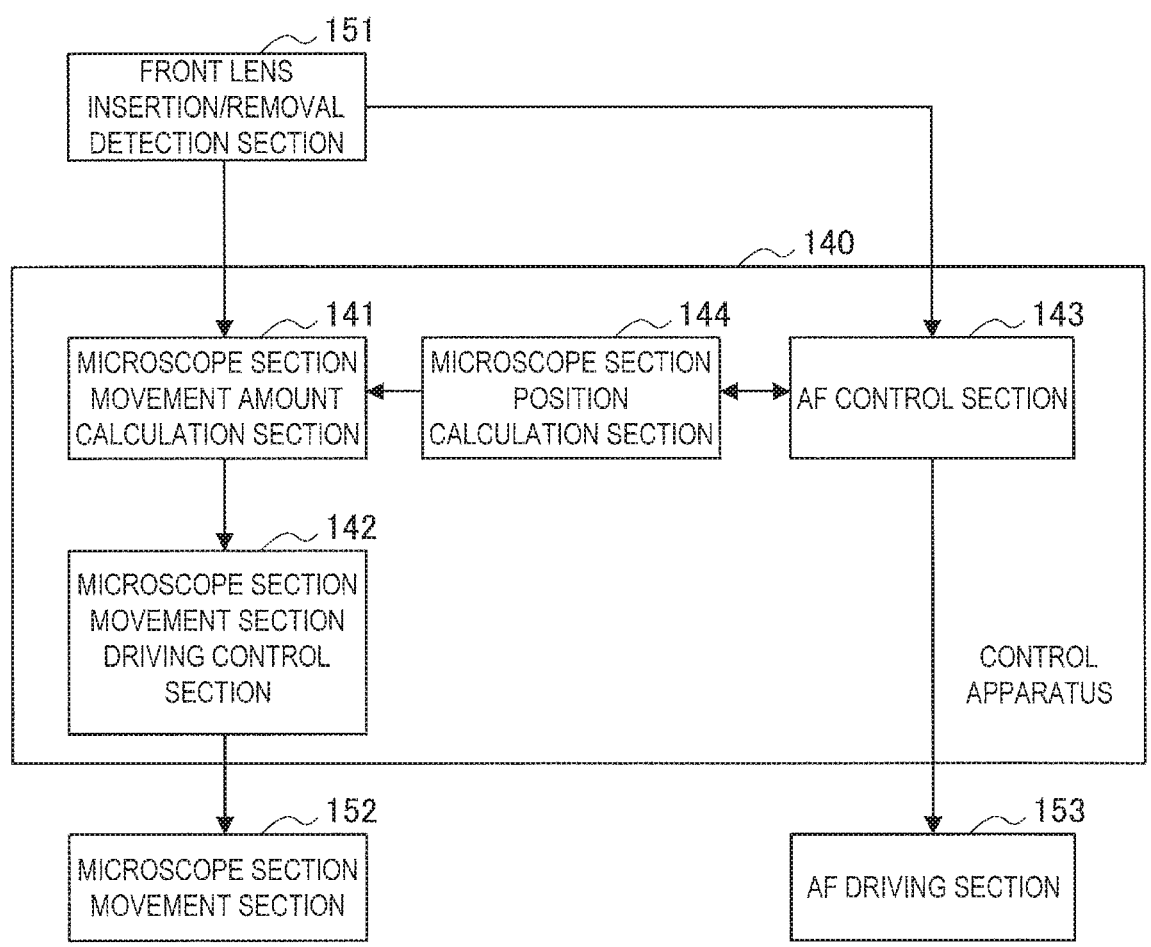
FIG. 2 is a function block diagram illustrating one example of a functional configuration of functions related to a refocusing process of a control apparatus according to the first embodiment.

FIG. 2 will be referenced to describe functions related to the refocusing process in the control apparatus 140 according to the first embodiment. FIG. 2 is a function block diagram illustrating one example of a functional configuration of functions related to the refocusing process of the control apparatus 140 according to the first embodiment. In FIG. 2, among the functions of the control apparatus 140, the functions related to the refocusing process are illustrated schematically as blocks.

Also, in FIG. 2, for the sake of explanation, a front lens insertion/removal detection section 151, a microscope section movement section 152, and an AF driving section 153 are illustrated together as function blocks outside the control apparatus 140. First, these functions will be described.

The front lens insertion/removal detection section 151 includes a function of detecting the insertion and removal of the front lens 131 on the optical axis by the front lens insertion/removal unit 130. Although omitted from illustration in FIG. 1, the microscope apparatus 10 is equipped with a detection apparatus for detecting the insertion and removal of the front lens 131 on the optical axis, and the front lens insertion/removal detection section 151 includes such a detection apparatus.

It is sufficient for the detection apparatus included in the front lens insertion/removal detection section 151 to be able to detect the insertion and removal of the front lens 131 on the optical axis, and the specific type of the detection apparatus is not limited. For example, the rotation axis section 133 of the front lens insertion/removal unit 130 may be provided with an encoder that detects the rotational angle, and the encoder may function as the front lens insertion/removal detection section 151. The detection value of the rotational angle of the rotation axis section 133 by the encoder expresses the rotational angle of the front lens holding member 132, and since the rotational angle may indicate the position of the front lens 131, by detecting the rotational angle, the insertion and removal of the front lens 131 on the optical axis may also be detected. Also, for example, a sensor that detects an object existing on the optical axis of the microscope section 110 preferably is provided, and the sensor preferably functions as the front lens insertion/removal detection section 151.

The front lens insertion/removal detection section 151 provides information indicating that the detected front lens 131 has been inserted onto the optical axis or information indicating that the front lens 131 has been removed from the optical axis to a microscope section movement amount calculation section 141 and an AF control section 143 of the control apparatus 140.

The microscope section movement section 152 includes a function of causing the microscope section 110 to move in the optical axis direction under control from a microscope section movement section driving control section 142 of the control apparatus 140. The microscope section movement section 152 includes the linear motion mechanism 122 illustrated in FIG. 1.

The AF driving section 153 includes a function of executing operations related to the AF function in the microscope section 110 under control from the AF control section 143 of the control apparatus 140 described later. The AF driving section 153 includes a driving mechanism that causes the focus lens of the optical system 113 provided in the microscope section 110 described with reference to FIG. 1 to move on the optical axis.

Next, the functions of the control apparatus 140 will be described. Referring to FIG. 2, functionally, the control apparatus 140 includes the microscope section movement amount calculation section 141, the microscope section movement section driving control section 142, the AF control section 143, and a microscope section position calculation section 144. These functions are achieved by a processor of the control apparatus 140 executing computational processing in accordance with a predetermined program.

When triggered by information indicating that the front lens 131 has been inserted onto the optical axis being transmitted from the front lens insertion/removal detection section 151, the microscope section movement amount calculation section 141 calculates the movement amount in the optical axis direction of the microscope section 110 from the current position (that is, the position at the point in time when the front lens 131 was inserted onto the optical axis) such that the front lens 131 will be positioned at the designed front lens position. As described above, in the microscope apparatus 10, since the distance in the optical axis direction between the microscope section 110 and the front lens 131 is kept constant, if the microscope section 110 is moved in the optical axis direction, the front lens 131 may also be moved in the optical axis direction.

As described later, the microscope section movement amount calculation section 141 is provided with information about the position in the optical axis direction of the microscope section 110 with respect to the subject's eye 401 at the point in time when the front lens 131 was inserted (hereinafter, this "information about the position in the optical axis direction of the microscope section 110 with respect to the subject's eye 401 at the point in time when the front lens 131 was inserted" will also be abbreviated to simply the "position information of the microscope section 110") from the microscope section position calculation section 144. Also, the distance from the subject's eye 401 of the designed front lens position and the distance in the vertical direction between the microscope section 110 and the front lens 131 are predetermined values, and in the first embodiment, information about these values is input into the control apparatus 140 in advance. On the basis of the information about these values and the position information of the microscope section 110, the microscope section movement amount calculation section 141 is able to calculate the movement amount in the optical axis direction of the microscope section 110 for moving the front lens 131 to the designed front lens position.

The microscope section movement amount calculation section 141 provides information about the calculated movement amount in the optical axis direction of the microscope section 110 to the microscope section movement section driving control section 142.

On the basis of the information about the movement amount in the optical direction of the microscope section 110 calculated by the microscope section movement amount calculation section 141, the microscope section movement section driving control section 142 causes the microscope section movement section 152 to operate (specifically, causes the actuator of the linear motion mechanism 122 of the holding section 120 to operate) such that the microscope section 110 moves by the movement amount. With this arrangement, the front lens 131 is moved in the optical axis direction to the designed front lens position.

The AF control section 143 executes control related to the AF function in the microscope section 110. The AF control section calculates the movement amount of the focus lens of the optical system 113 such that the focal point is aligned with a predetermined position in accordance with a predetermined method related to AF. Additionally, by controlling the operations of the AF driving section 153 to cause the focus lens to move by the calculated movement amount, AF operation is executed. In the first embodiment, the AF method is not limited, and either of an active method and a passive method may be used. Also, in the case in which a passive method is used, any of various known types of methods may be applied, such as a phase difference detection method or a contrast method, for example.

When observing the anterior of the subject's eye 401, the AF control section 143 causes the microscope section 110 to execute AF operation such that the focal point is aligned with the anterior eye. Note that at this time, the AF control section 143 provides information about the focal length of the microscope section 110 when observing the anterior of the subject's eye 401 to the microscope section position calculation section 144.

On the other hand, in the case in which information indicating that the front lens 131 has been inserted onto the optical axis is transmitted from the front lens insertion/removal detection section 151, the AF control section 143 causes the microscope section 110 to execute AF operation such that the focal point is aligned with the image-forming position of the fundus image by the front lens 131. At this time, the AF control section 143 causes AF operation to be executed after waiting for the front lens 131 to be moved to the designed front lens position by the microscope section movement section driving control section 142.

Herein, in the first embodiment, as described above, the front lens 131 is moved to the designed front lens position by the microscope section movement section driving control section 142. At this time, since the image-forming position of the fundus image by the front lens 131 should be aligned with the designed fundus image position 403, ideally, in the microscope section 110, if refocusing is executed such that the focal point is aligned with the designed fundus image position 403, a clear fundus image should be obtained, and executing AF operation is unnecessary. However, in actuality, due to factors such as positioning error when moving the front lens 131 and individual differences in the characteristics (such as the size and optical characteristics) of the subject's eye 401, the image-forming position of the fundus image by the front lens 131 after moving sometimes is misaligned slightly from the designed fundus image position 403. Consequently, as above, it is necessary to cause AF operation to be executed by the AF control section 143 such that the focal point is aligned with the image-forming position of the true fundus image.

Note at this time, since the image-forming position of the true fundus image may exist near the designed fundus image position 403, the AF control section 143 does not have to cause AF operation to be executed over the entire adjustable range of the focal length, and it is sufficient to execute AF operation intended for refocusing near the designed fundus image position 403. With this arrangement, refocusing may be executed efficiently, and it becomes possible to execute the refocusing process in a shorter time. As described later, the position information of the microscope section 110 is provided to the AF control section 143 from the microscope section position calculation section 144. Also, the distance from the subject's eye 401 of the designed fundus image position 403 is itself a predetermined value, and in the first embodiment, information about the value is input into the control apparatus 140 in advance. The AF control section 143 is able to cause AF operation intended for refocusing near the designed fundus image position 403 to be executed on the basis of the information about the value of the distance from the subject's eye 401 of the designed fundus image position 403 and the position information of the microscope section 110.

The microscope section position calculation section 144 calculates the position in the optical axis direction of the microscope section 110 with respect to the subject's eye 401 at the point in time when the front lens 131 was inserted, on the basis of the information about the focal length of the microscope section 110 when observing the anterior of the subject's eye 401 provided from the AF control section 143. Specifically, since the structure of the microscope section 110 is known, if the focal length of the microscope section 110 when observing the anterior of the subject's eye 401 is understood, it is possible to calculate the WD of the microscope section 110 with respect to the anterior eye, or in other words, the position in the optical axis direction of the microscope section 110 with respect to the subject's eye 401. Parameters about the structure of the microscope section 110 are input into the control apparatus 140 in advance, and the microscope section position calculation section 144 is able to calculate the position in the optical axis direction of the microscope section 110 with respect to the subject's eye 401 at the point in time when the front lens 131 was inserted, on the basis of the parameters and the information about the focal length of the microscope section 110 when observing the anterior of the subject's eye 401.

The microscope section position calculation section 144 provides information about the calculated position in the optical axis direction of the microscope section 110 with respect to the subject's eye 401 at the point in time when the front lens 131 was inserted to the microscope section movement amount calculation section 141 and the AF control section 143.

The above describes the function of adjusting the focal length in the control apparatus 140. As described above, according to the first embodiment, in the case in which the front lens 131 is inserted onto the optical axis, the refocusing process for observing the fundus image clearly is executed by the control apparatus 140 automatically. Consequently, since it is not necessary to execute the refocusing process manually, medical staff are freed from troublesome work, and in addition, it becomes possible to improve surgical efficiency further.

Note that although the above description describes the case in which the front lens 131 is inserted onto the optical axis, in the microscope apparatus 10, even in the case in which the front lens 131 is removed from the optical axis, similarly, the refocusing process for obtaining an image of the anterior eye clearly may be executed automatically by the control apparatus 140. In this case, it is sufficient for the control apparatus 140 to cause the each of the microscope section movement section 152 and the AF driving section 153 to operate by the microscope section movement section driving control section 142 and the AF control section 143 to revert the position in the optical axis direction of the front lens 131 and the focal length of the microscope section 110 to the state before the front lens 131 was inserted onto the optical axis.

Also, in the above description, the refocusing process is executed automatically when the front lens 131 is inserted onto the optical axis, but the first embodiment is not limited to such an example. In the first embodiment, in addition to the refocusing process, other processes for clearly obtaining the fundus image additionally may be executed automatically. For example, in the case in which the microscope section 110 includes an AE function, when the front lens 131 is inserted onto the optical axis, the control apparatus 140 may also adjust the exposure of the microscope section 110 by the AE function according to the brightness of the fundus image formed by the front lens 131. Also, it is known that when the front lens 131 is inserted onto the optical axis, the observation image will become an inverse image that is inverted up and down as well as left and right. Consequently, in the case in which the front lens 131 is inserted onto the optical axis, the control apparatus 140 may also execute a process of converting the inverse image to a correct image automatically. The conversion process preferably is executed together when executing the image processing on the image signal acquired by the microscope section 110. Note that even for the exposure adjustment and the image conversion, processes that revert back to the original state preferably are executed automatically in the case in which the front lens 131 is removed from the optical axis.

Also, in the above description, the holding section 120 includes the stand 121 and the linear motion mechanism 122, but the first embodiment is not limited to such an example. In the first embodiment, the holding section 120 may be configured in any way insofar as the microscope section 110 is movable in the optical axis direction. For example, the holding section 120 preferably is configured as a multi-link structure in which multiple links are successively joined via multiple rotation axis sections. If the multi-link structure is configured to have at least six degrees of freedom for the motion of the microscope section 110 on the front end, it becomes possible to hold the microscope section 110 at any position and in any attitude within the movable range of the multi-link structure, thereby allowing the multi-link structure to substitute for the illustrated configuration of the holding section 120.

Also, in the above description, when calculating the position in the optical axis direction of the microscope section 110 with respect to the subject's eye 401 at the point in time when the front lens 131 was inserted, the microscope section position calculation section 144 calculates the position of the microscope section 110 on the basis of the information about the focal length of the microscope section 110 when observing the anterior of the subject's eye 401, but the first embodiment is not limited to such an example. In the first embodiment, the method by which the microscope section position calculation section 144 calculates the position of the microscope section 110 is not limited, and any method may be applied as the method. For example, the microscope apparatus 10 may be provided with a distance sensor that detects the distance from the microscope section 110 of an object on the optical axis. In this case, the microscope section position calculation section 144 is able to calculate the position of the microscope section 110 on the basis of a value detected by the distance sensor.

Also, in the above description, the microscope section 110 is an electronic imaging microscope section, but the first embodiment is not limited to such an example. In the first embodiment, the microscope section 110 may also be an optical microscope section with which the surgeon performs magnified observation of a surgical site through the optical system by peering into the microscope section directly from an eyepiece. In this case, the method of the AF function provided in the microscope section 110 is limited to an active method, but it is possible to execute the refocusing process automatically, similarly to the case of an electronic imaging microscope section.

However, the electronic imaging microscope apparatus 10 is able to enjoy the following advantages compared to a microscope apparatus provided with an optical microscope section (hereinafter also called an optical microscope apparatus). For example, in the electronic imaging microscope apparatus 10, since the adjustable range of the focal length is large, the changeable range of the WD of the microscope section 110 may also be increased, making it possible to dispose the microscope section 110 with a high degree of freedom during observation. Also, since functions such as an AE function and an electronic zoom function are providable in addition to the AF function, convenience for the surgeon may be improved further. Furthermore, since it is possible to configure the microscope section 110 more compactly, the microscope apparatus 10 overall may be reduced in size. In consideration of these advantages, the use of the electronic imaging microscope apparatus 10 may be said to be preferable.

Also, in the refocusing process according to the first embodiment, the AF function in the microscope section 110 is utilized, but typically, in an electronic imaging microscope section like the microscope section 110, an AF function is provided often compared to an optical microscope section. Consequently, by using the electronic imaging microscope section 110, it becomes possible to execute the refocusing process according to the first embodiment without providing an additional configuration and function for AF. Given this point as well, in the first embodiment, the use of the microscope section 110 may be said to be more preferable than an optical microscope section.

(1-3. Control Method)

Figure 3:
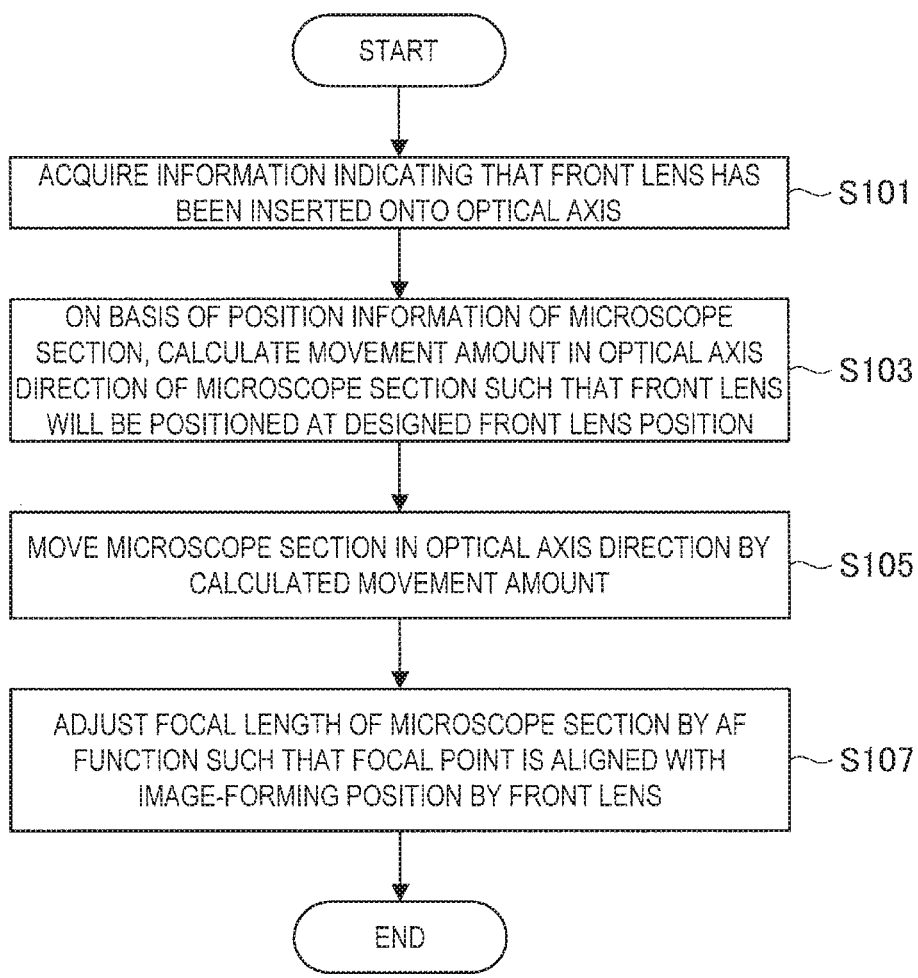
FIG. 3 is a flowchart illustrating one example of a processing procedure of a control method of the microscope apparatus related to the refocusing process according to the first embodiment.

FIG. 3 will be referenced to described a processing procedure of the control method of the microscope apparatus 10 related to the refocusing process according to the first embodiment executed by the control apparatus 140 described above. FIG. 3 is a flowchart illustrating one example of a processing procedure of the control method of the microscope apparatus 10 related to the refocusing process according to the first embodiment. Note that each process illustrated in FIG. 3 corresponds to each process executed by the control apparatus 140 illustrated in FIG. 2, and by having a processor included in the control apparatus 140 execute computational processing in accordance with a predetermined program, each process illustrated in FIG. 3 may be executed. Since the details of each process illustrated in FIG. 3 have already been described above in the description of the functions of the control apparatus 140, in the following description of the processing procedure of the control method, an overview of each process will be described briefly, and detailed description will be omitted.

Referring to FIG. 3, in the control method of the microscope apparatus 10 related to the refocusing process according to the first embodiment, first, information indicating that the front lens 131 has been inserted onto the optical axis is acquired (step S101). The process in step S101 corresponds to the process described with reference to FIG. 3, in which information indicating that the front lens 131 has been inserted onto the optical axis is input into the control apparatus 140 from the front lens insertion/removal detection section 151.

Next, on the basis of the position information of the microscope section 110, the movement amount in the optical axis direction of the microscope section 110 such that the front lens 131 will be positioned at the designed front lens position is calculated (step S103). The process in step S103 corresponds the process executed by the microscope section movement amount calculation section 141 illustrated in FIG. 3.

Next, the microscope section 110 is moved in the optical axis direction by the calculated movement amount (step S105). The process in step S105 corresponds the process executed by the microscope section movement section driving control section 142 illustrated in FIG. 3.

Next, the focal length of the microscope section 110 is adjusted by the AF function such that the focal point is aligned with the image-forming position by the front lens 131 (step S107). The process in step S107 corresponds to the process executed by the AF control section 143 illustrated in FIG. 3.

The above describes a processing procedure of the control method of the microscope apparatus 10 related to the function of adjusting the focal length according to the first embodiment.

(1-4. Modifications)

In the exemplary configuration described above, the distance in the optical axis direction between the microscope section 110 and the front lens 131 is kept at a fixed value. However, the first embodiment is not limited to such an example. The microscope apparatus 10 may also be configured such that the distance in the optical axis direction between the microscope section 110 and the front lens 131 is variable.

Like the exemplary configuration described above, in the case in which the distance in the optical axis direction between the microscope section 110 and the front lens 131 is fixed, by adjusting the distance between the front lens 131 and the subject's eye 401 to a predetermined value, the WD of the microscope section 110 during fundus observation becomes fixed. In contrast, if the distance in the optical axis direction between the microscope section 110 and the front lens 131 is variable, even in the case in which the distance between the front lens 131 and the subject's eye 401 is adjusted to a predetermined value, by appropriately adjusting the distance in the optical axis direction between the microscope section 110 and the front lens 131, it becomes possible to change the WD of the microscope section 110. Herein, as one modification of the first embodiment, such a microscope apparatus in which the distance in the optical axis direction between the microscope section 110 and the front lens 131 is variable and a control method of such a microscope apparatus will be described.

Herein, as described above, a feature of the electronic imaging microscope section 110 is that the WD can be changed relatively freely. Consequently, in eye surgery using the microscope apparatus 10, depending on the surgical conditions, there may exist demand to take advantage of this feature and perform surgery while freely changing the WD of the microscope section 110. Regarding this point, in the exemplary configuration described above, although the WD of the microscope section 110 can be changed freely during observation of the anterior eye, the WD becomes fixed during fundus observation. In contrast, in the present modification, it becomes possible to change the WD of the microscope section 110 freely even during fundus observation, thereby making it possible to meet the above demand and further improve convenience for the surgeon. In this way, according to the present modification, smooth surgery is realized similarly to the exemplary configuration described above, while in addition, an advantageous effect of further improving convenience for the surgeon is obtained.

(1-4-1. Overall Configuration of Microscope Apparatus)

Since the configuration of the microscope apparatus according to the present modification is substantially the same as the microscope apparatus 10 described with reference to FIG. 1, a detailed description will be omitted for the duplicate configuration herein. However, in the microscope apparatus according to the present modification, the configuration of the front lens insertion/removal unit 130 and the configuration of the control apparatus 140 are different from the microscope apparatus 10.

Specifically, the front lens insertion/removal unit according to the present modification has substantially the same configuration as the front lens insertion/removal unit 130 illustrated in FIG. 1, but is configured such that the position in the optical axis direction of the front lens 131 with respect to the microscope section 110 is changeable. Specifically, in the present modification, the front lens insertion/removal unit has a configuration in which the front lens 131 is held on the front end of a front lens holding member, similarly to the front lens insertion/removal unit 130 illustrated in FIG. 1. However, although the front lens holding member has substantially the same configuration as the front lens holding member 132 illustrated in FIG. 1, the multiple links are configured to be rotatably joined to each other by a rotation axis section. The rotation axis section is provided with an actuator, and by driving the actuator under control from a control apparatus 240 described later, the angle between the links included in the front lens holding member may be changed, and the position in the optical axis direction of the front lens 131 with respect to the microscope section 110, or in other words the distance between the microscope section 110 and the front lens 131, may be changed.

Also, in the present modification, the control apparatus 240 is provided instead of the control apparatus 140 illustrated in FIG. 1. The configuration and functions of the control apparatus 240 are similar to the control apparatus 140 except in relation to the refocusing process when inserting or removing the front lens 131. Hereinafter, the differences from the control apparatus 140, namely, the functions related to the refocusing process in the control apparatus 240 according to the present modification will be described in detail.

(1-4-2. Functional Configuration of Control Apparatus)

Figure 4:
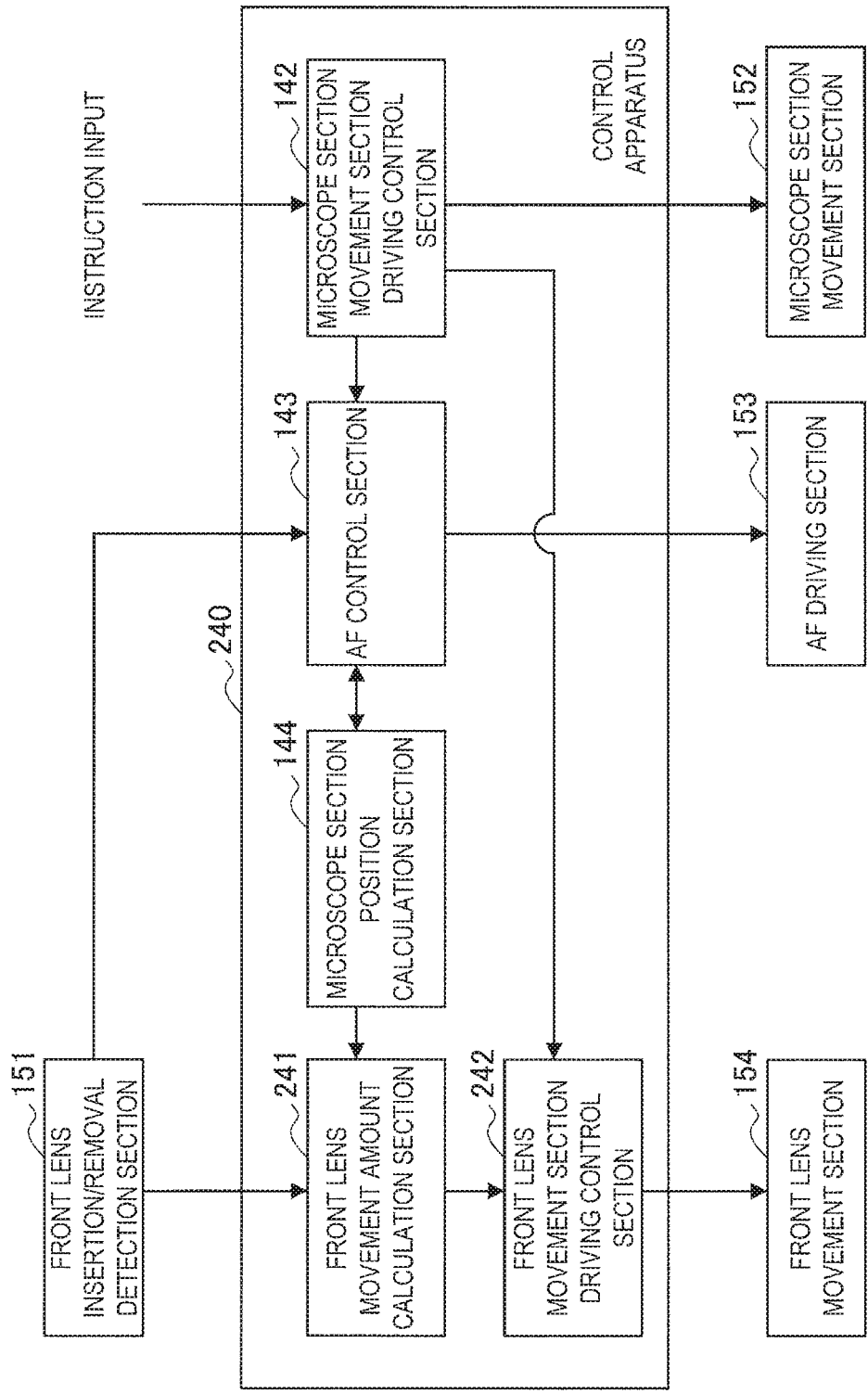
FIG. 4 is a function block diagram illustrating one example of a functional configuration of functions related to a refocusing process of a control apparatus according to a modification of the first embodiment.

FIG. 4 will be referenced to describe functions related to the refocusing process in the control apparatus 240 according to a modification of the first embodiment. FIG. 4 is a function block diagram illustrating one example of a functional configuration of functions related to the refocusing process of the control apparatus 240 according to a modification of the first embodiment. In FIG. 4, among the functions of the control apparatus 240, the functions related to the refocusing process are illustrated schematically as blocks.

Also, in FIG. 4, for the sake of explanation, the front lens insertion/removal detection section 151, the microscope section movement section 152, the AF driving section 153, and a front lens movement section 154 are illustrated together as function blocks outside the control apparatus 240. Of these, since the functions of the front lens insertion/removal detection section 151, the microscope section movement section 152, and the AF driving section 153 are similar to these functions illustrated in FIG. 2, a description will be omitted here. However, in the present modification, the front lens insertion/removal detection section 151 provides information indicating that the detected front lens 131 has been inserted onto the optical axis or information indicating that the front lens 131 has been removed from the optical axis to a front lens movement amount calculation section 241 and the AF control section 143 of the control apparatus 240.

The front lens movement section 154 includes a function of moving the front lens 131 in the optical axis direction under control from a front lens movement section driving control section 242 of the control apparatus 240. The front lens movement section 154 includes the rotation axis section included in the front lens holding member described above.

Referring to FIG. 4, functionally, the control apparatus 240 includes the front lens movement amount calculation section 241, the front lens movement section driving control section 242, the microscope section movement section driving control section 142, the AF control section 143, and the microscope section position calculation section 144. These functions are achieved by a processor of the control apparatus 240 executing computational processing in accordance with a predetermined program.

When triggered by information indicating that the front lens 131 has been inserted onto the optical axis being transmitted from the front lens insertion/removal detection section 151, the front lens movement amount calculation section 241 calculates the movement amount in the optical axis direction of the front lens 131 from the current position (that is, the position at the point in time when the front lens 131 was inserted onto the optical axis) such that the front lens 131 will be positioned at the designed front lens position.

As described later, the position information of the microscope section 110 is provided to the front lens movement amount calculation section 241 from the microscope section position calculation section 144. Also, the front lens insertion/removal unit according to the present modification is configured such that an initial position in the optical axis direction of the front lens 131 with respect to the microscope section 110 at the point in time of the state with the front lens 131 inserted onto the optical axis becomes a predetermined position. The distance from the subject's eye 401 of the designed front lens position and the initial position in the optical axis direction of the front lens 131 are predetermined values, and in the present modification, information about these values is input into the control apparatus 240 in advance. On the basis of the information about these values and the position information of the microscope section 110, the front lens movement amount calculation section 241 calculates the movement amount in the optical axis direction of the front lens 131 for moving the front lens 131 to the designed front lens position.

The front lens movement amount calculation section 241 provides information about the calculated movement amount in the optical axis direction of the front lens 131 to the front lens movement section driving control section 242.

On the basis of the information about the movement amount in the optical axis direction of the front lens 131 calculated by the front lens movement amount calculation section 241, the front lens movement section driving control section 242 causes the front lens movement section 154 to operate (specifically, causes the actuator provided in the rotation axis section included in the front lens holding member of the front lens holding member to operate) such that the front lens 131 moves by the movement amount. With this arrangement, the front lens 131 is moved in the optical axis direction to the designed front lens position.

Herein, in the present modification, as described later, during fundus observation, the microscope section 110 is able to move in the optical axis direction in accordance with instruction input by the surgeon. As described later, information about the movement amount of the microscope section 110 is provided to the front lens movement section driving control section 242 from the microscope section movement section driving control section 142, and on the basis of the information and the position information of the microscope section 110 provided from the microscope section position calculation section 144, the front lens movement section driving control section 242 causes the front lens movement section 154 to operate such that the front lens 131 continues to be positioned at the designed front lens position, even in the case in which the microscope section 110 moves.

The function of the AF control section 143 is substantially similar to the function in FIG. 2 described above. That is, when observing the anterior of the subject's eye 401, the AF control section 143 causes the microscope section 110 to execute AF operation such that the focal point is aligned with the anterior eye. At this time, the AF control section 143 provides information about the focal length of the microscope section 110 when observing the anterior of the subject's eye 401 to the microscope section position calculation section 144.

On the other hand, in the case in which information indicating that the front lens 131 has been inserted onto the optical axis is transmitted from the front lens insertion/removal detection section 151, the AF control section 143 causes the microscope section 110 to execute AF operation such that the focal point is aligned with the image-forming position of the fundus image by the front lens 131. At this time, the AF control section 143 causes AF operation to be executed after waiting for the front lens 131 to be moved to the designed front lens position by the front lens movement section driving control section 242.

Since the front lens 131 is moved to the designed front lens position by the front lens movement section driving control section 242, ideally, in the microscope section 110, if refocusing is executed such that the focal point is aligned with the designed fundus image position 403, a clear fundus image should be obtained, and executing AF operation is unnecessary. However, similarly to the case of the control apparatus 140 described above, in actuality, because of various factors, the image-forming position of the fundus image by the front lens 131 after moving sometimes is misaligned slightly from the designed fundus image position 403, and as above, it is necessary for the AF operation to be executed by the AF control section 143 such that the focal point is aligned with the image-forming position of the true fundus image.

Note that at this time, similarly to the case of the control apparatus 140, the position information of the microscope section 110 is provided to the AF control section 143 from the microscope section position calculation section 144. Consequently, the AF control section 143 is able to grasp the distance from the microscope section 110 to the designed fundus image position 403 on the basis of the above information and the information about the distance from the subject's eye 401 of the designed front lens position input into the control apparatus 240 in advance, and cause AF operation intended for refocusing near the designed fundus image position 403 to be executed. With this arrangement, refocusing may be executed efficiently, and it becomes possible to execute the refocusing process in a shorter time.

Also, in the present modification, as described later, during fundus observation, the microscope section 110 is able to move in the optical axis direction in accordance with instruction input by the surgeon. In the case in which such movement of the microscope section 110 occurs, the AF control section 143 continues to cause the AF driving section 153 to execute the AF operation for aligning the focal point with the image-forming position of the fundus image by the front lens 131. With this arrangement, even in the case in which the microscope section 110 moves, a clear fundus image is continually captured by the microscope section 110. Note that at this point, as described later, information about the movement amount of the microscope section 110 is provided to the AF control section 143 from the microscope section movement section driving control section 142, and on the basis of the information and the position information of the microscope section 110 provided from the microscope section position calculation section 144, the AF control section 143 is able to continuously calculate the distance in the vertical direction between the microscope section 110 and the designed fundus image position 403, and thereby continue to cause the AF operation intended for refocusing near the designed fundus image position 403 to be executed.

The function of the microscope section movement section driving control section 142 is substantially the same as the function in FIG. 2 described above. However, in the present modification, during fundus observation, the microscope section movement section driving control section 142 does not cause the microscope section 110 to move automatically, but rather causes the microscope section movement section 152 to operate (specifically, causes the actuator of the linear motion mechanism 122 of the holding section 120 to operate) in accordance with instruction input by the surgeon to move the microscope section 110 in the optical axis direction by an amount according to the instruction input. In this way, in the present modification, during not only observation of the anterior eye but also during fundus observation, it is possible to dispose the microscope section 110 at a free position on the optical axis within the range of the WD according to instruction input by the surgeon. When causing the microscope section 110 to move in accordance with instruction input by the surgeon, the microscope section movement section driving control section 142 provides information about the movement amount of the microscope section 110 to the front lens movement section driving control section 242 and the AF control section 143.

The function of the microscope section position calculation section 144 is substantially the same as the function in FIG. 2 described above. In other words, the microscope section position calculation section 144 calculates the position in the optical axis direction of the microscope section 110 with respect to the subject's eye 401 at the point in time when the front lens 131 was inserted, on the basis of the information about the focal length of the microscope section 110 when observing the anterior of the subject's eye 401 provided from the AF control section 143. The microscope section position calculation section 144 provides information about the calculated position in the optical axis direction of the microscope section 110 with respect to the subject's eye 401 at the point in time when the front lens 131 was inserted to the front lens movement amount calculation section 241 and the AF control section 143.

The above describes the functions related to the refocusing process of the control apparatus 240. As described above, according to the present modification, similarly to the exemplary configuration described above, the refocusing process in the case in which the front lens 131 is inserted onto the optical axis is executed automatically. Consequently, smoother surgery may be realized. Also, according to the present modification, it becomes possible to change the WD of the microscope section 110 freely, not only during observation of the anterior eye but also during fundus observation. Consequently, convenience for the surgeon may be improved further.

Note that when the front lens 131 is inserted onto the optical axis and the front lens 131 is moved to the designed front lens position by the front lens movement section driving control section 242, depending on the position in the optical axis direction of the microscope section 110 when observing the anterior eye, at that position of the microscope section 110, it may not be possible to move the front lens 131 to the designed front lens position in some cases. For example, in some cases, during observation of the anterior eye, the WD of the microscope section 110 is small and the designed front lens position exists above the objective lens of the microscope section 110, and in some cases, during observation of the anterior eye, the WD of the microscope section 110 is large and the designed front lens position exists farther away from the microscope section 110 than the movable distance in the optical axis direction of the front lens 131 with respect to the microscope section 110. In such cases, to cause the front lens 131 to move to the designed front lens position, the front lens movement section driving control section 242 may cause the microscope section movement section 152 to operate through the microscope section movement section driving control section 142, and thereby cause the microscope section 110 to move appropriately in the optical axis direction to a predetermined position such that the designed front lens position is included within the movable range in the optical axis direction of the front lens 131 with respect to the microscope section 110.

(1-4-3. Control Method)

Figure 5:
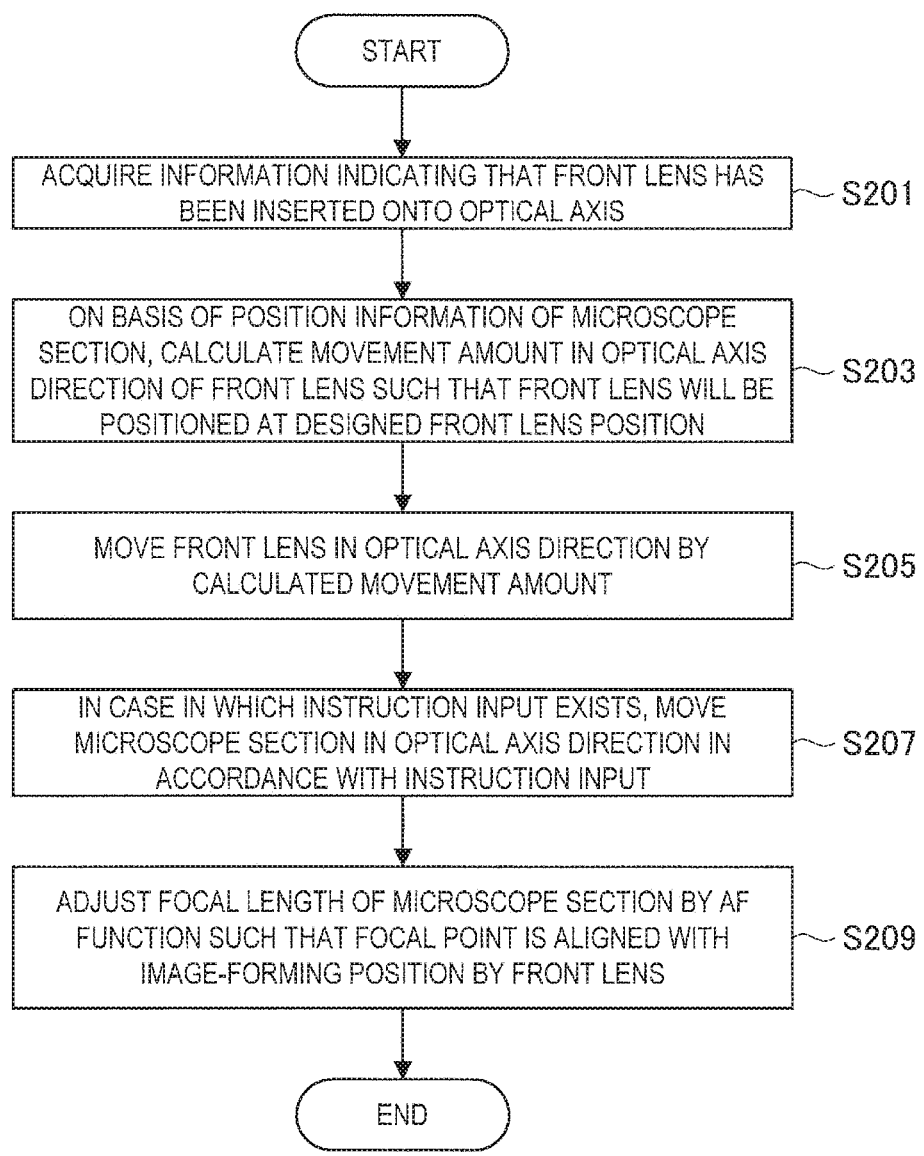
FIG. 5 is a flowchart illustrating one example of a processing procedure of a control method of the microscope apparatus related to the refocusing process according to a modification of the first embodiment.

FIG. 5 will be referenced to described a processing procedure of the control method of the microscope apparatus related to the refocusing process according to a modification of the first embodiment executed by the control apparatus 240 described above. FIG. 5 is a flowchart illustrating one example of a processing procedure of the control method of the microscope apparatus related to the refocusing process according to a modification of the first embodiment. Note that each process illustrated in FIG. 5 corresponds to each process executed by the control apparatus 240 illustrated in FIG. 4, and by having a processor included in the control apparatus 240 execute computational processing in accordance with a predetermined program, each process illustrated in FIG. 5 may be executed. Since the details of each process illustrated in FIG. 5 have already been described above in the description of the functions of the control apparatus 240, in the following description of the processing procedure of the control method, an overview of each process will be described briefly, and detailed description will be omitted.

Referring to FIG. 5, in the control method of the microscope apparatus related to the refocusing process according to one modification of the first embodiment, first, information indicating that the front lens 131 has been inserted onto the optical axis is acquired (step S201). The process in step S201 is a process similar to the process in step S101 illustrated in FIG. 3.

Next, on the basis of the position information of the microscope section 10, the movement amount in the optical axis direction of the front lens 131 such that the front lens 131 will be positioned at the designed front lens position is calculated (step S203). The process in step S203 corresponds the process executed by the front lens movement amount calculation section 241 illustrated in FIG. 5.

Next, the front lens 131 is moved in the optical axis direction by the calculated movement amount (step S205). The process in step S205 corresponds the process executed by the front lens movement section driving control section 242 illustrated in FIG. 5.

Next, in the case in which there is instruction input from the surgeon, the microscope section 110 is moved in the optical axis direction in accordance with the instruction input (step S207). The process in step S207 corresponds the process executed by the microscope section movement section driving control section 142 illustrated in FIG. 5. Note that in the case in which there is no instruction input from the surgeon, step S207 is skipped.

Next, the focal length of the microscope section 110 is adjusted by the AF function such that the focal point is aligned with the image-forming position by the front lens 131 (step S209). At this point, in the case in which the microscope section 110 is moving in accordance with instruction input from the surgeon in step S207, the focal length of the microscope section 110 may be adjusted on the basis of the information about the movement amount of the microscope section 110. The process in step S209 corresponds to the process executed by the AF control section 143 illustrated in FIG. 5.

The above describes a processing procedure of the control method of the microscope apparatus related to the refocusing process according to one modification of the first embodiment.

Figure 6:
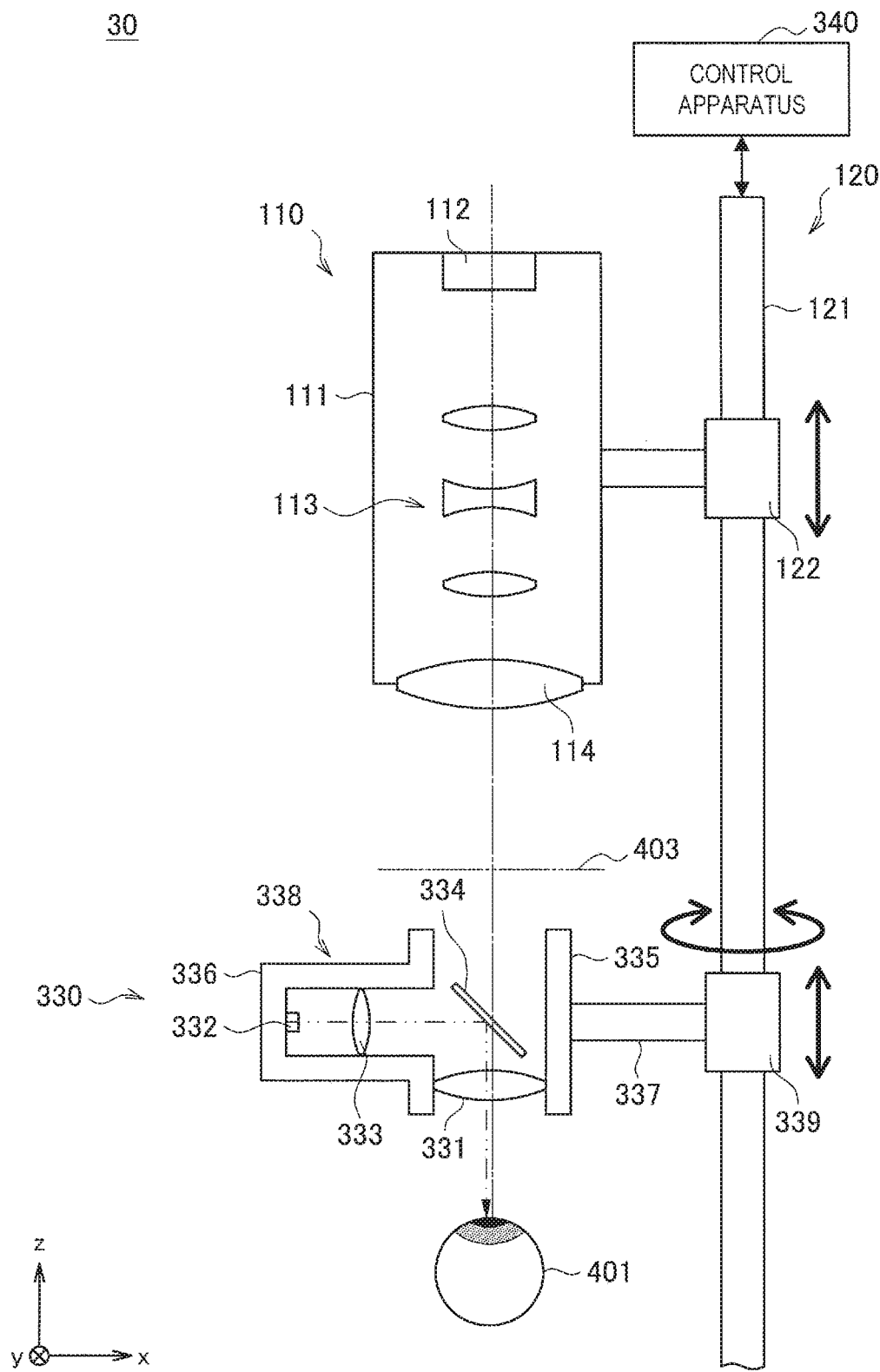
FIG. 6 is a diagram illustrating a schematic configuration of a microscope apparatus according to a second embodiment.

FIG. 6 will be referenced to describe a configuration of the microscope apparatus according to the second embodiment. FIG. 6 is a diagram schematically illustrating a configuration of the microscope apparatus according to the second embodiment.

Referring to FIG. 6, the microscope apparatus 30 according to the second embodiment is provided with a microscope section 110 for performing magnified observation of a subject's eye 401, an arm section 120 (holding section 120) that holds the microscope section 110, a front lens insertion/removal unit 330 that inserts or removes a front lens on the optical axis of the microscope section 110, and a control apparatus 340 that centrally controls the operations of the microscope apparatus 30. Note that in FIG. 6, similarly to the microscope apparatus 10 illustrated in FIG. 1, the microscope apparatus 30 is described as one in which the microscope section 110 is disposed directly above the subject's eye 401 such that the optical axis is parallel to an approximately vertical direction.

Since the configurations and functions of the microscope section 110 and the holding section 120 are similar to the configurations and functions of these members in the first embodiment, a detailed description is omitted here. However, as described above, in the second embodiment, since the front lens insertion/removal unit 330 is provided with a light source 332 of illuminating light, the microscope section 110 is not provided with the light source.

The front lens insertion/removal unit 330 includes a front lens 331, the light source 332 of illuminating light, an illumination optical system 333, a half-mirror 334, a front lens holding member 338 that holds the front lens 331, the light source 332, the illumination optical system 333, and the half-mirror 334 on the front end side, and a rotation axis section 339, interposed between the base end of the front lens holding member 338 and the stand 121 of the holding section 120, that rotatably supports the front lens holding member 338 treating the base end of the front lens holding member 338 as a base point and the vertical direction with respect to the stand 121 as a rotation axis. In this way, in the second embodiment, the front lens insertion/removal unit 330 is attached to the stand 121 and configured separately from the microscope section 110.

The front lens 331 has a configuration and function similar to the front lens 131 in the first embodiment.

The light source 332 is a light-emitting diode (LED) or a laser diode (LD) for example, and emits light of a predetermined intensity and a predetermined wavelength under control from the control apparatus 340.

The illumination optical system 333 includes a function of guiding emitted light from the light source 332 to the outside while also adjusting the characteristics of the emitted light to desired characteristics suited to observation of the fundus. In the illustrated example, a single lens is illustrated as the illumination optical system 333 for the sake of convenience, but the illumination optical system 333 may also include multiple lenses or a combination of a lens and various other optical elements.

The half-mirror 334 directs the forward direction of the emitted light from the light source 332 passing through the illumination optical system 333 downward, and also aligns the optical axis of the emitted light with the optical axis of the microscope section 110 in a state in which the front lens 331 is inserted onto the optical axis of the microscope section 110.

The front lens holding member 338 mainly includes three members (first member 335, second member 336, and third member 337). The first member 335 and the second member 336 have hollow cylindrical shapes of different sizes. The first member 335 of large diameter is disposed such that its central axis is approximately parallel to the vertical direction. The first member 335 is open on both ends, and the front lens 331 is fitted into the lower opening.

The second member 336 of small diameter is disposed such that its central axis is approximately parallel to the horizontal direction, and the second member 336 is positioned with respect to the first member 335 such that one end abuts a side wall of the first member 335. The site of abutment with the second member 336 on the side wall of the first member 335 is provided with an opening, and the interiors of the first member 335 and the second member 336 are in communication through the opening. The other end of the second member 336 is closed. In this way, by combining the first member 335 and the second member 336, a single housing is configured. In other words, the housing has a shape in which a cylinder of smaller diameter (that is, the second member 336) is connected to a side face of a cylinder of larger diameter (that is, the first member 335) such that its central axis is appropriately perpendicular to the side face.

The light source 332 is disposed in the closed-end portion of the second member 336 inside the housing, and the illumination optical system 333 is disposed downstream from the light source 332 in the interior of the second member 336. In the interior of the first member 335 inside the housing, the half-mirror 334 is disposed at a position corresponding to the intersection point between the central axis of the first member 335 and the central axis of the second member 336. The half-mirror 334 is disposed to direct the forward direction of the emitted light from the light source 332 passing through the illumination optical system 333 downward, and also align the optical axis of the emitted light with the optical axis of the microscope section 110 in the state in which the front lens 131 is inserted onto the optical axis of the microscope section 110. According to such a configuration, in the state in which the front lens 131 is inserted, the emitted light (that is, illuminating light) from the light source 332 directed downward by the half-mirror 334 passes through the front lens 331 and enters the subject's eye 401. In FIG. 6, the optical path of the illuminating light is denoted schematically with an arrow. Of the illuminating light, reflected light (that is, observation light) from the subject's eye 401 passes through the front lens 331 and the half-mirror 334, continues to proceed upward, and enters the microscope section 110.

The third member 337 of the front lens holding member 338 is an elongated member, one end of which is securely connected to the side face of the first member 335 on the opposite side of the side where the second member 336 exists. The other end of the third member 337 is rotatably held by the rotation axis section 339 with respect to the stand 121 treating the vertical direction as the rotation axis direction. Note that in this specification, in the front lens holding member 338, the side connected to the stand 121 (that is, the side where the third member 337 is positioned) is also designated the base end side, while the opposite side (that is, the side where the second member 336 is positioned) is also designated the front end side.

By having the third member 337 rotate with respect to the stand 121 via the rotation axis section 339 treating the vertical direction as the rotation axis direction, the housing including the first member 335 and the second member 336 as well as the members inside (that is, the entirety of the front lens insertion/removal unit 330) rotates treating the vertical direction as the rotation axis direction. By such a rotation operation, the insertion and removal of the front lens 331 on the optical axis of the microscope section 110 is realized (FIG. 6 illustrates a situation in which the front lens 331 is inserted onto the optical axis).

The rotation axis section 339 is provided with an actuator, and by driving the actuator under control from the control apparatus 340, the rotation axis section 339 operates, and the rotation of the front lens insertion/removal unit 330, or in other words, the insertion and removal of the front lens 331 on the optical axis, is executed.

Note that in the second embodiment, the position in the vertical direction of the rotation axis section 339 (that is, the position in the vertical direction of the front lens insertion/removal unit 330) may be configured to be movable manually or electrically via an actuator or the like. For example, before surgery, the height of the operating table, the height of the subject's eye 401 from the top face of the operating table when the patient lies supine on top of the operating table, the size of the subject's eye 401, and the like may be taken into consideration and the position in the vertical direction of the front lens insertion/removal unit 330 may be adjusted such that when the front lens 331 is inserted onto the optical axis, the image-forming position of the fundus image by the front lens 331 is aligned with the designed fundus image position 403 (that is, the front lens 331 is positioned at the designed front lens position). In the case in which the movement in the vertical direction of the front lens insertion/removal unit 330 is executed electrically, the movement preferably is executed under control from the control apparatus 340.

The control apparatus 340 includes a processor such as a CPU or a DSP, or a control board or the like on which these processors and a storage element such as memory are mounted together. As a result of a processor included in the control apparatus 340 executing computational processing in accordance with a predetermined program, each function in the control apparatus 340 is realized. Note that in FIG. 6, to avoid complexity in the drawing, an arrow is drawn between the control apparatus 340 and the stand 121 of the holding section 120 to denote the connection between the two for the sake of convenience, but in actuality, the control apparatus 340 is connected to each member of the microscope apparatus 30 to allow the exchange of various information by any of various known types of wired or wireless communication methods.

Regarding the functions of the control apparatus 340, the control of the operation of the microscope section 110 (for example, adjustment of the magnification, focal length, and the like), the control of the display of the image captured by the microscope section 110, and the control of the operation of the holding section 120 (for example, the operation of the linear motion mechanism 122) are similar to these functions of the control apparatus 140 in the first embodiment.

As a function different from that of the first embodiment, the control apparatus 340 includes a function of controlling the operations of the front lens insertion/removal unit 330. Specifically, by causing the rotation axis section 339 to operate and causing the front lens holding member 338 of the front lens insertion/removal unit 330 to rotate with respect to the microscope section 110, the control apparatus 340 executes the insertion or removal of the front lens 331 on the optical axis.

The control of the microscope section 110, the holding section 120, the front lens insertion/removal unit 330, and the display apparatus (not illustrated) that displays the image captured by the microscope section 110 by the control apparatus 340 described above is executed in accordance with instruction input by the surgeon, for example. The microscope apparatus 30 is provided with an input apparatus such as a footswitch and a touch panel not illustrated, and by having the surgeon perform various types of instruction input through the input apparatus, the control apparatus 340 causes each configuration above to operate in accordance with the instruction input.

Herein, in the second embodiment, similarly to the first embodiment, to obtain a clear fundus image, it is also necessary to execute a process of refocusing the microscope section 110 in response to the insertion of the front lens 331 onto the optical axis by the front lens insertion/removal unit 330. In the second embodiment, when the front lens 331 is inserted onto the optical axis, the refocusing process is executed automatically under control from the control apparatus 340.

Hereinafter, functions related to the refocusing process in the control apparatus 340 will be described in detail.

(2-2. Functional Configuration of Control Apparatus)

Figure 7:
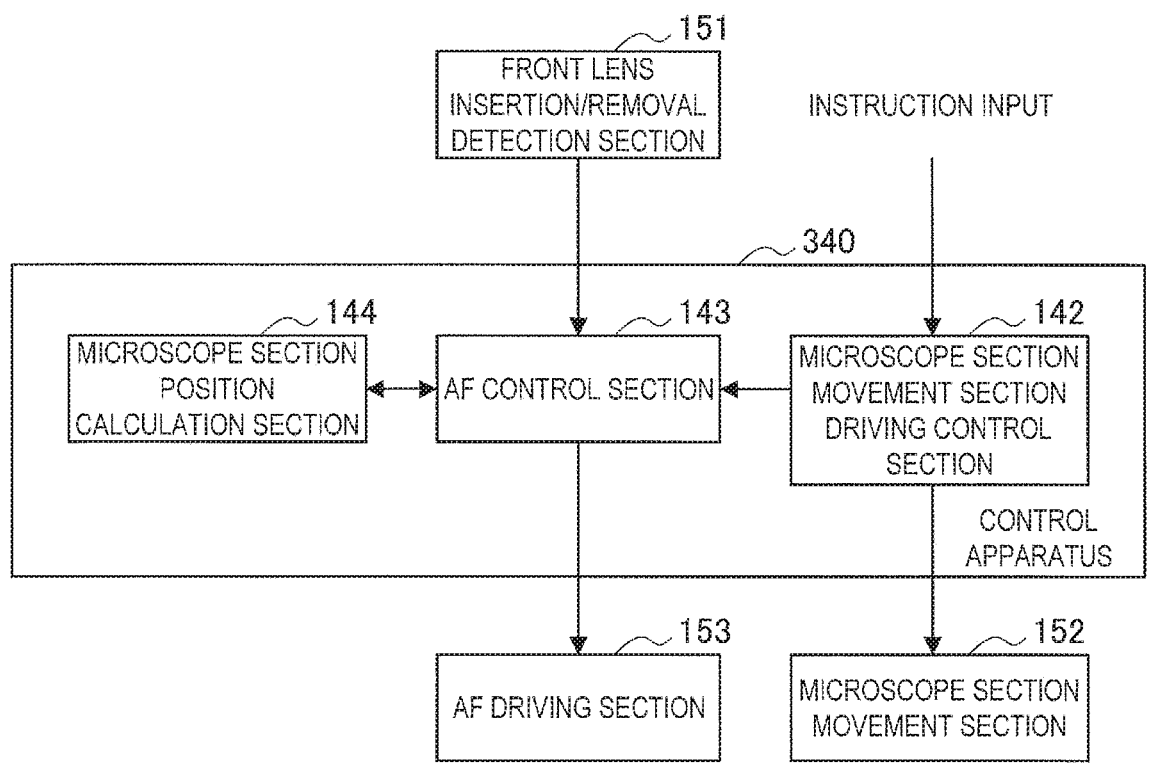
FIG. 7 is a function block diagram illustrating one example of a functional configuration of functions related to a refocusing process of a control apparatus according to the second embodiment.

FIG. 7 will be referenced to describe functions related to the refocusing process in the control apparatus 340 according to the second embodiment. FIG. 7 is a function block diagram illustrating one example of a functional configuration of functions related to the refocusing process of the control apparatus 340 according to the second embodiment. In FIG. 7, among the functions of the control apparatus 340, the functions related to the refocusing process are illustrated schematically as blocks.

Also, in FIG. 7, for the sake of explanation, a front lens insertion/removal detection section 151, a microscope section movement section 152, and an AF driving section 153 are illustrated together as function blocks outside the control apparatus 340. Since these functions are similar to these functions in the first embodiment illustrated in FIG. 2, a description is omitted here. However, according to the second embodiment, the front lens insertion/removal detection section 151 provides information indicating that the detected front lens 331 has been inserted onto the optical axis or information indicating that the front lens 331 has been removed from the optical axis to an AF control section 143 of the control apparatus 340.

Referring to FIG. 7, functionally, the control apparatus 340 includes the microscope section movement section driving control section 142, the AF control section 143, and a microscope section position calculation section 144. These functions are achieved by a processor of the control apparatus 340 executing computational processing in accordance with a predetermined program.

The function of the AF control section 143 is substantially the same as the function of the first embodiment illustrated in FIG. 2 described above. That is, when observing the anterior of the subject's eye 401, the AF control section 143 causes the microscope section 110 to execute AF operation such that the focal point is aligned with the anterior eye. At this time, the AF control section 143 provides information about the focal length of the microscope section 110 when observing the anterior of the subject's eye 401 to the microscope section position calculation section 144.

On the other hand, in the case in which information indicating that the front lens 331 has been inserted onto the optical axis is transmitted from the front lens insertion/removal detection section 151, the AF control section 143 causes the microscope section 110 to execute AF operation such that the focal point is aligned with the image-forming position of the fundus image by the front lens 331. Herein, in the first embodiment described above, since the process of moving the front lens 131 to the designed front lens position in the optical axis direction is executed after the front lens 131 is inserted onto the optical axis, it is necessary for the AF control section 143 to stand by without executing AF operation until the process ends. In contrast, in the second embodiment, as described above, since the position in the vertical direction of the front lens insertion/removal unit 330 is adjusted in advance, at the point in time when the front lens 331 is inserted onto the optical axis by the front lens insertion/removal unit 330, the front lens 331 is already positioned at the designed front lens position. Consequently, unlike the first embodiment, it is not necessary to execute the process of moving the front lens 331 in the optical axis direction, and when the front lens 331 is inserted onto the optical axis, the control of AF operation by the AF control section 143 may be executed immediately. Therefore, it becomes possible to execute the refocusing process associated with the insertion of the front lens 331 onto the optical axis in a shorter time and more smoothly than the first embodiment.

Note that, as above, since the front lens 331 is positioned at the designed front lens position at the point in time when the front lens front lens 331 is inserted onto the optical axis, ideally; in the microscope section 110, if refocusing is executed such that the focal point is aligned with the designed fundus image position 403, a clear fundus image should be obtained, and executing AF operation is unnecessary. However, in actuality, due to factors such as changes in the posture of the patient, for example, there is a risk that the image-forming position of the fundus image by the front lens 331 after insertion onto the optical axis will be misaligned slightly from the designed fundus image position 403. Consequently, as above, it is necessary to cause AF operation to be executed by the AF control section 143 such that the focal point is aligned with the image-forming position of the true fundus image.

Note that at this time, similarly to the case of the control apparatus 140, the position information of the microscope section 110 is provided to the AF control section 143 from the microscope section position calculation section 144. Consequently, the AF control section 143 is able to grasp the distance from the microscope section 110 to the designed fundus image position 403 at the point of time when the front lens 331 is inserted onto the optical axis on the basis of the above information and the information about the distance from the subject's eye 401 of the designed front lens position input into the control apparatus 340 in advance. Similar to the first embodiment, the AF control section 143, using the above information, is able to cause AF operation intended for refocusing near the designed fundus image position 403 to be executed. With this arrangement, refocusing may be executed efficiently, and it becomes possible to execute the refocusing process in a shorter time.

Also, in the second embodiment, as described later, during fundus observation, the microscope section 110 is able to move in accordance with instruction input by the surgeon. In the case in which such movement of the microscope section 110 occurs, similar to the modification of the first embodiment, the AF control section 143 continues to cause the AF driving section 153 to execute the AF operation for aligning the focal point with the image-forming position of the fundus image by the front lens 331. With this arrangement, even in the case in which the microscope section 110 moves, a clear fundus image is continually captured by the microscope section 110. Note that at this point, as described later, information about the movement amount of the microscope section 110 is provided to the AF control section 143 from the microscope section movement section driving control section 142, and on the basis of the information and the position information of the microscope section 110 provided from the microscope section position calculation section 144, the AF control section 143 is able to continuously calculate the distance in the vertical direction between the microscope section 110 and the designed fundus image position 403, and thereby continue to cause the AF operation intended for refocusing near the designed fundus image position 403 to be executed.

The function of the microscope section movement section driving control section 142 is substantially the same as the function of the first embodiment described above. However, in the second embodiment, similar to the modification of the first embodiment, during fundus observation, the microscope section movement section driving control section 142 does not cause the microscope section 110 to move automatically, but rather causes the microscope section movement section 152 to operate (specifically, causes the actuator of the linear motion mechanism 122 of the holding section 120 to operate) in accordance with instruction input by the surgeon to move the microscope section 110 by an amount according to the instruction input. In this way, in the second embodiment, during not only observation of the anterior eye but also during fundus observation, it is possible to dispose the microscope section 110 at a free position on the optical axis within the range of the WD according to instruction input by the surgeon. When causing the microscope section 110 to move in accordance with instruction input by the surgeon, the microscope section movement section driving control section 142 provides information about the movement amount of the microscope section 110 to the AF control section 143.

The function of the microscope section position calculation section 144 is substantially the same as the function of the first embodiment described above. In other words, the microscope section position calculation section 144 calculates the position in the optical axis direction of the microscope section 110 with respect to the subject's eye 401 at the point in time when the front lens 331 was inserted, on the basis of the information about the focal length of the microscope section 110 when observing the anterior of the subject's eye 401 provided from the AF control section 143. The microscope section position calculation section 144 provides information about the calculated position in the optical axis direction of the microscope section 110 with respect to the subject's eye 401 at the point in time when the front lens 331 was inserted to the AF control section 143.

The above describes the functions related to the refocusing process of the control apparatus 340. As described above, according to the second embodiment, similarly to the first embodiment, the refocusing process in the case in which the front lens 331 is inserted onto the optical axis is executed automatically. Consequently, smoother surgery may be realized. Also, according to the second embodiment, similar to the modification of the first embodiment, it becomes possible to change the WD of the microscope section 110 freely, not only during observation of the anterior eye but also during fundus observation. Consequently, convenience for the surgeon may be improved further. Furthermore, according to the second embodiment, since the front lens 331 is already positioned at the designed front lens position at the point in time when the front lens 331 is inserted onto the optical axis by the front lens insertion/removal unit 330, it is not necessary to execute the process of moving the front lens 331 in the optical axis direction to adjust its position, and when the front lens 331 is inserted onto the optical axis, the control of AF operation by the AF control section 143 may be executed immediately. Consequently, it becomes possible to execute the refocusing process associated with the insertion of the front lens 331 onto the optical axis in a shorter time and more smoothly than the first embodiment.

At this point, typically, in an electronic imaging microscope apparatus, it is desirable to make the microscope smaller and lighter for reasons such as making the microscope apparatus more compact and securing the field of view for the surgeon who looks at a display apparatus. Given such circumstances, in the first embodiment, since the microscope section 110 is equipped with the front lens insertion/removal unit 130 as well as a light source and an illumination optical system, there are concerns regarding increased size and weight of the microscope section 110. On the other hand, in the second embodiment, as described above, the front lens insertion/removal unit 330 is configured separately from the microscope section 110. Also, the front lens insertion/removal unit 330 is equipped with the light source 332 and the illumination optical system 333, while the microscope section 110 is not equipped with these configurations. Consequently, according to the second embodiment, it becomes possible to potentially reduce the size of the microscope section 110.

However, in the second embodiment above, the microscope section 110 is not equipped with the light source 332 and the illumination optical system 333, but in cases in which the following circumstances exist, these configurations may also be provided in both the microscope section 110 and the front lens insertion/removal unit 330. Typically, in a microscope apparatus, because the target site of observation is different, the front lens is interposed, and the like, the characteristics demanded of the illuminating light when observing the anterior eye and when observing the fundus are different in some cases. Consequently, in a microscope apparatus, sometimes there is demand to provide multiple light sources. In this case, in the first embodiment, if multiple light sources are provided in the microscope section 110, there are concerns regarding increased size of the microscope section 110. On the other hand, if the number of light sources to provide is limited simply to reduce the size of the microscope section 110, it becomes difficult to achieve clear observation for both the anterior eye and the fundus.

In contrast, according to the second embodiment, the light source 332 and the illumination optical system 333 are provided in the front lens insertion/removal unit 330, and the illuminating light from these configurations irradiates the subject's eye 401 only during fundus observation. Consequently, in the second embodiment, by equipping the microscope section 110 with a light source and an illumination optical system suited to observation of the anterior eye and equipping the front lens insertion/removal unit 330 with the light source 332 and the illumination optical system 333 suited to observation of the fundus, it becomes possible to switch the illuminating light according to the observation target without increasing the size of the microscope section 110 more than necessary. In this way, in cases in which there is demand to switch the illuminating light according to the target site of observation while also keeping the microscope section 110 compact, in the second embodiment, the microscope section 110 preferably is also provided with a light source and an illumination optical system.

Note that, as described above, in the second embodiment, the position in the vertical direction of the rotation axis section 339 of the front lens insertion/removal unit 330 may be configured to be movable manually or electrically via an actuator or the like. In the above description, such a function is used in advance before surgery to adjust the position in the vertical direction of the front lens insertion/removal unit 330, or in other words, the position on the optical axis of the front lens 331 when the front lens 331 is inserted onto the optical axis, but the second embodiment is not limited to such an example. For example, even if adjustment is performed in advance, various factors could conceivably cause a situation in which the position on the optical axis of the front lens 331 becomes misaligned from the designed front lens position when the front lens 331 is inserted onto the optical axis. In the case in which such a situation occurs, when the front lens 331 is inserted onto the optical axis, the control apparatus 340 may also cause the rotation axis section 339, or in other words the front lens insertion/removal unit 330, to move in the vertical direction in accordance with instruction input by the surgeon, such that the front lens 331 is positioned at the designed front lens position. In this way, the movement in the vertical direction of the front lens insertion/removal unit 330 may not only be performed in advance, but may also be performed as necessary during fundus observation in accordance with instruction input by the surgeon.

(2-3. Control Method)

Figure 8:
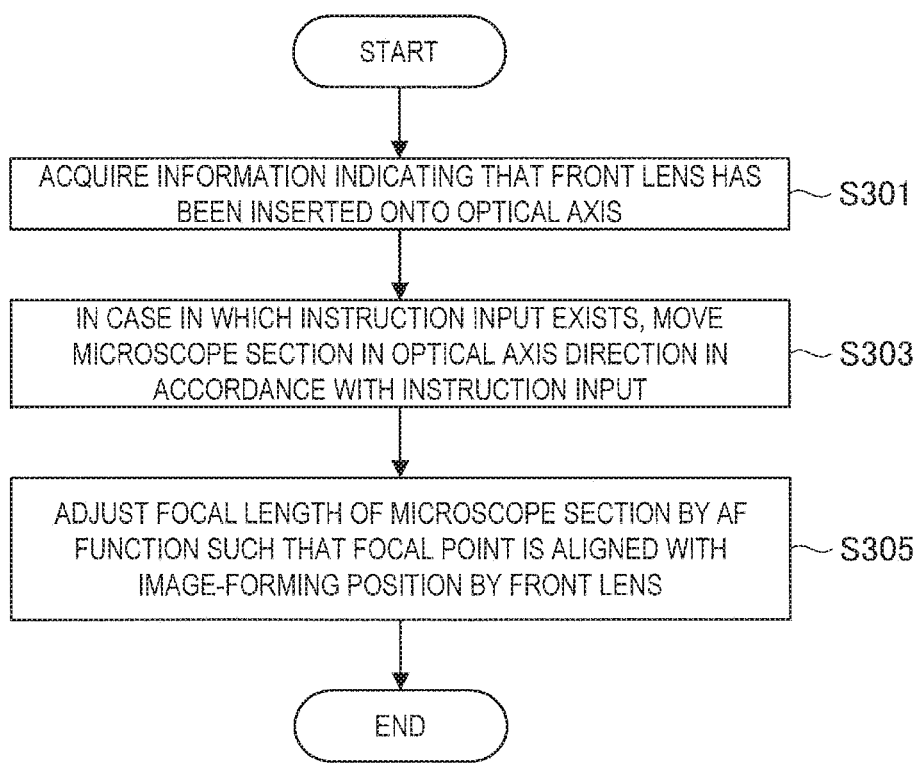
FIG. 8 is a flowchart illustrating one example of a processing procedure of a control method of the microscope apparatus related to the refocusing process according to the second embodiment.

FIG. 8 will be referenced to described a processing procedure of the control method of the microscope apparatus 30 related to the refocusing process according to the second embodiment executed by the control apparatus 340 described above. FIG. 8 is a flowchart illustrating one example of a processing procedure of the control method of the microscope apparatus 30 related to the refocusing process according to the second embodiment. Note that each process illustrated in FIG. 8 corresponds to each process executed by the control apparatus 340 illustrated in FIG. 7, and by having a processor included in the control apparatus 340 execute computational processing in accordance with a predetermined program, each process illustrated in FIG. 8 may be executed. Since the details of each process illustrated in FIG. 8 have already been described above in the description of the functions of the control apparatus 340, in the following description of the processing procedure of the control method, an overview of each process will be described briefly, and detailed description will be omitted.

Referring to FIG. 8, in the control method of the microscope apparatus 30 related to the refocusing process according to the second embodiment, first, information indicating that the front lens 331 has been inserted onto the optical axis is acquired (step S301). The process in step S301 is a process similar to the process in step S101 of the control method according to the first embodiment illustrated in FIG. 3.

Next, in the case in which there is instruction input from the surgeon, the microscope section 110 is moved in the optical axis direction in accordance with the instruction input (step S303). The process in step S303 corresponds the process executed by the microscope section movement section driving control section 142 illustrated in FIG. 7. Note that in the case in which there is no instruction input from the surgeon, step S303 is skipped.

Next, the focal length of the microscope section 110 is adjusted by the AF function such that the focal point is aligned with the image-forming position by the front lens 131 (step S305). At this point, in the case in which the microscope section 110 is moving in accordance with instruction input from the surgeon in step S303, the focal length of the microscope section 110 may be adjusted on the basis of the information about the movement amount of the microscope section 110. The process in step S305 corresponds to the process executed by the AF control section 143 illustrated in FIG. 7.

The above describes a processing procedure of the control method of the microscope apparatus 30 related to the refocusing process according to the second embodiment.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, each configuration in each embodiment described above may be combined with each other where possible. For example, the various configurations (such as executing exposure adjustment and image conversion processing when inserting the front lens 131 onto the optical axis, reverting the focal length and the like to the original state when removing the front lens 131 from the optical axis, the method of acquiring the position information of the microscope section 110 by the microscope section position calculation section 144, and the types of microscope sections) described as modifications in (1-2. Functional configuration of control apparatus) above may also be applied in the microscope apparatus 30 according to the second embodiment.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A microscope apparatus including:
a microscope section configured to image a subject's eye with an image sensor for performing magnified observation of the subject's eye:
a holding section configured to hold the microscope section;
a front lens insertion/removal unit configured to insert/remove a front lens for observing a posterior eye of the subject's eye onto an optical axis of the microscope section: and
a control apparatus configured to execute an AF control that focuses the microscope section on an image-forming position of an image of the posterior eye by the front lens when the front lens is inserted onto the optical axis of the microscope section by the front lens insertion/removal unit.

(2)

The microscope apparatus according to (1), in which
when the front lens is inserted onto the optical axis of the microscope section by the front lens insertion/removal unit, the front lens is disposed such that the front lens is positioned at a predetermined designed front lens position at which a distance to the subject's eye is a predetermined distance.

(3)

The microscope apparatus according to (2), in which
the control apparatus executes the AF control intended to refocus near a designed posterior eye image position that is an image-forming position of an image of the posterior eye by the front lens in a case in which the front lens is disposed at the designed front lens position.

(4)

The microscope apparatus according to (2) or (3), in which
the front lens insertion/removal unit includes the front lens, a front lens holding member that holds the front lens on a front end, and a rotation axis section interposed between a base end of the front lens holding member and the microscope section that rotatably supports the front lens holding member with respect to the microscope section by treating the base end of the front lens holding member as a base point.

(5)

The microscope apparatus according to (4), in which
the holding section includes a microscope section movement section configured to move the microscope section in an optical axis direction of the microscope section,
the front lens insertion/removal unit is configured such that when the front lens is inserted onto the optical axis of the microscope section, a distance in the optical axis direction of the microscope section between the microscope section and the front lens becomes fixed, and
when the front lens is inserted onto the optical axis of the microscope section by the front lens insertion/removal unit, the control apparatus causes the microscope section to be moved in the optical axis direction of the microscope section by the microscope section movement section, thereby adjusting a position in the optical axis direction of the microscope section of the front lens such that the front lens is positioned at the designed front lens position.

(6)

The microscope apparatus according to (4), in which
the front lens insertion/removal unit is configured such that a length of the front lens holding member is variable, and when the front lens is inserted onto the optical axis of the microscope section, a distance in the optical axis direction of the microscope section between the microscope section and the front lens is changeable, and
when the front lens is inserted onto the optical axis of the microscope section by the front lens insertion/removal unit, the control apparatus causes the front lens holding member to operate and changes the distance in the optical axis direction of the microscope section of the front lens with respect to the microscope section, thereby adjusting a position in the optical axis direction of the microscope section of the front lens such that the front lens is positioned at the designed front lens position.

(7)

The microscope apparatus according to (2) or (3), in which
the front lens insertion/removal unit includes the front lens, a front lens holding member that holds the front lens on a front end, and a rotation axis section interposed between a base end of the front lens holding member and the holding section that rotatably supports the front lens holding member with respect to the holding section by treating the base end of the front lens holding member as a base point.

(8)

The microscope apparatus according to (7), in which
the rotation axis section is configured to be movable on the holding section, and
by moving the rotation axis section on the holding section to move the front lens holding member under control from the control apparatus, the position in the optical axis direction of the microscope section of the front lens is adjusted.

(9)

The microscope apparatus according to (7) or (8), in which
the front lens insertion/removal unit is provided with a light source configured to emit illuminating light at the subject's eye.

(10)

The microscope apparatus according to any one of (1) to (9), in which
when the front lens is inserted onto the optical axis of the microscope section by the front lens insertion/removal unit, the control apparatus executes an AE control that an exposure in the microscope section to an exposure corresponding to a brightness of an image of the posterior eye formed by the front lens.

(11)

The microscope apparatus according to any one of (1) to (10), in which
when the front lens is inserted onto the optical axis of the microscope section by the front lens insertion/removal unit, the control apparatus executes a process of converting from an inverse image to a correct image in which an image of the posterior eye captured by the front lens is inverted up and down as well as left and right.

(12)

A control method, executed by a processor, including:
when performing magnified observation of a subject's eye using a microscope apparatus provided with a microscope section configured to image the subject's eye with an image sensor for performing magnified observation of the subject's eye, a holding section configured to hold the microscope section, and a front lens insertion/removal unit configured to insert/remove a front lens for observing a posterior eye of the subject's eye onto an optical axis of the microscope section, executing an AF control that focuses the microscope section on an image-forming position of an image of the posterior eye by the front lens when the front lens is inserted onto the optical axis of the microscope section by the front lens insertion/removal unit.

REFERENCE SIGNS LIST 10, 30 microscope apparatus
110 microscope section
111 housing
112 image sensor
113 optical system
114 objective lens
120 holding section (arm section)
121 stand
122 linear motion mechanism
130, 330 front lens insertion/removal unit
131, 331 front lens
132 front lens holding member
133 rotation axis section
140, 240, 340 control apparatus
141 microscope section movement amount calculation section
142 microscope section movement section driving control section
143 AF control section
144 microscope section position calculation section
151 front lens insertion/removal detection section
152 microscope section movement section
153 AF driving section
154 front lens movement section
241 front lens movement amount calculation section
242 front lens movement section driving control section
332 light source
333 illumination optical system
334 half-mirror
335 first member
336 second member
337 third member
338 front lens holding member
339 rotation axis section
401 subject's eye
403 designed fundus image position

The invention claimed is:

1. A microscope system comprising:
a microscope configured to image a subject's eye with an image sensor;
a holding arm configured to hold the microscope;
a front lens support configured to insert/remove a front lens for observing a posterior of the subject's eye onto an optical axis of the microscope; and
circuitry, when the posterior of the subject's eye is to be imaged, configured to:
move at least one of the microscope and the front lens relative to one another along the optical axis direction of the microscope, thereby adjusting a position in the optical axis direction of the microscope of the front lens such that the front lens is positioned at a designed front lens position at which a distance to the subject's eye is a predetermined distance in a case where the front lens is inserted onto the optical axis of the microscope by the front lens support, and
execute an auto-focus control that focuses the microscope on an image-forming position of an image of the posterior of the subject's eye by the front lens when the front lens is inserted onto the optical axis of the microscope at the designed front lens position by the front lens support.

2. The microscope system according to claim 1, wherein circuitry is configured to execute the auto-focus control intended to refocus near a designed posterior eye image position that is an image-forming position of an image of the posterior eye by the front lens in a case in which the front lens is disposed at the designed front lens position.

3. The microscope system according to claim 1, wherein the front lens support includes the front lens, a front lens holding member that holds the front lens on a front end, and a rotation axis section interposed between a base end of the front lens holding member and the microscope that rotatably supports the front lens holding member with respect to the microscope section by treating the base end of the front lens holding member as a base point.

4. The microscope system according to claim 3, wherein the holding arm includes a microscope translator configured to move the microscope in the optical axis direction of the microscope,
the front lens support is configured such that when the front lens is inserted onto the optical axis of the microscope, a distance in the optical axis direction of the microscope between the microscope and the front lens becomes fixed, and
when the front lens is inserted onto the optical axis of the microscope by the front lens support, the circuitry is configured to move the microscope in the optical axis direction of the microscope by the microscope translator such that the front lens is positioned at the designed front lens position.

5. The microscope system according to claim 3, wherein the front lens support is configured such that a length of the front lens holding member is variable, and when the front lens is inserted onto the optical axis of the microscope, a distance in the optical axis direction of the microscope between the microscope and the front lens is changeable, and
when the front lens is inserted onto the optical axis of the microscope by the front lens support, the circuitry is configured to operate the front lens holding member to change the distance in the optical axis direction of the microscope of the front lens with respect to the microscope such that the front lens is positioned at the designed front lens position.

6. The microscope system according to claim 1, wherein the front lens support includes the front lens, a front lens holding member that holds the front lens on a front end, and a rotation axis section interposed between a base end of the front lens holding member and the holding arm that rotatably supports the front lens holding member with respect to the holding arm by treating the base end of the front lens holding member as a base point.

7. The microscope system according to claim 6, wherein the rotation axis section is configured to be movable on the holding arm, and the circuitry is configured to move the rotation axis section on the holding arm to move the front lens holding member to adjust the position in the optical axis direction of the microscope of the front lens.

8. The microscope system according to claim 6, wherein the front lens support includes a light source configured to emit illuminating light at the subject's eye.

9. The microscope system according to claim 1, wherein when the front lens is inserted onto the optical axis of the microscope by the front lens support the circuitry is configured to execute an auto-focus control that an exposure in the microscope to an exposure corresponding to a brightness of an image of the posterior of the subject's eye formed by the front lens.

10. The microscope system according to claim wherein when the front lens is inserted onto the optical axis of the microscope by the front lens support, the circuitry is configured to convert an inverse image to a correct image in which an image of the posterior of the subject's eye captured by the front lens is inverted up and down as well as left and right.

11. The microscope system according to claim 1, wherein the circuitry is configured to move at least one of the microscope and the front lens relative to one another before the front lens is inserted onto the optical axis of the microscope by the front lens support.

12. The microscope system according to claim 1, wherein the circuitry is configured to move at least one of the microscope and the front lens relative to one another after the front lens is inserted onto the optical axis of the microscope by the front lens support.

13. A control method, executed by a processor, comprising:
performing magnified observation of a subject's eye using a microscope to image the subject's eye with an image sensor for performing magnified observation of an anterior of the subject's eye;
performing magnified observation of a posterior of the subject's eye with the image sensor for performing magnified observation, performing magnified observation of the posterior of the subject's eye including
inserting a front lens onto an optical axis of the microscope,
moving at least one of the microscope and the front lens relative to one another along the optical axis direction of the microscope, thereby adjusting a position in the optical axis direction of the microscope of the front lens such that the front lens is positioned at a designed front lens position at which a distance to the subject's eye is at a predetermined distance in a case where the front lens is inserted onto the optical axis of the microscope, and
executing auto-focus control that focuses the microscope on an image-forming position of an image of the posterior by the front lens when the front lens is inserted onto the optical axis of the microscope at the designed front lens position.

14. The control method according to claim 13, wherein moving at least one of the microscope and the front lens relative to one another is before inserting the front lens onto the optical axis of the microscope.

15. The control method according to claim 13, wherein moving at least one of the microscope and the front lens relative to one another is after inserting the front lens onto the optical axis of the microscope.

16. A controller for use with microscope apparatus including a microscope for imaging an anterior and a posterior of a subject's eye, the controller comprising:
circuitry, when the posterior of the subject's eye is to be imaged, configured to:
insert a front lens onto an optical axis of the microscope,
move the microscope and the front lens relative to one another along the optical axis direction of the microscope, thereby adjusting a position in the optical axis direction of the microscope of the front lens such that the front lens is positioned at a designed front lens position at which a distance to the subject's eye is at a predetermined distance in a case where the front lens is inserted onto the optical axis of the microscope, and
execute auto-focus control that focuses the microscope on an image-forming position of an image of the posterior of the subject's eye by the front lens in a case where the front lens is inserted onto the optical axis of the microscope at the designed front lens position.

17. The controller according to claim 16, wherein the circuitry is configured to move at least one of the microscope and the front lens relative to one another before the front lens is inserted onto the optical axis of the microscope by a front lens support on which the front lens is mounted.

18. The controller according to claim 16, wherein the circuitry is configured to move at least one of the microscope and the front lens relative to one another after the front lens is inserted onto the optical axis of the microscope by a front lens support on which the front lens is mounted.

* * * * *